United States Patent
Fletcher et al.

(10) Patent No.: US 10,679,746 B1
(45) Date of Patent: Jun. 9, 2020

(54) SYSTEMS AND METHODS FOR GENERATING AUTOMATED REAL-TIME GRAPHICAL USER INTERFACES

(71) Applicant: TeleTracking Technologies, Inc., Pittsburgh, PA (US)

(72) Inventors: Rodger J Fletcher, Gibsonia, PA (US); Prabhuvel Kandaswamy, Bridgeville, PA (US); Raghuram Ramesh, McDonald, PA (US); Jason Harber, Pittsburgh, PA (US); Benjamin Joel Martin, Harmony, PA (US); Ranjit Abbadasari, Pittsburgh, PA (US); Jaimin Patel, Monroeville, PA (US); Thomas Perry, Dubois, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 15/390,086

(22) Filed: Dec. 23, 2016

Related U.S. Application Data

(63) Continuation-in-part of application No. 14/950,463, filed on Nov. 24, 2015.
(Continued)

(51) Int. Cl.
*G06Q 50/00* (2012.01)
*G16H 40/63* (2018.01)
*G06F 19/00* (2018.01)

(52) U.S. Cl.
CPC ......... *G16H 40/63* (2018.01); *G06F 19/3418* (2013.01)

(58) Field of Classification Search
USPC .......................................... 705/2–4
See application file for complete search history.

(56) References Cited

U.S. PATENT DOCUMENTS

| 8,204,832 B2 | 6/2012 | Minagawa et al. |
| 8,401,870 B2 * | 3/2013 | Whelchel ............... G06Q 10/06 705/2 |

(Continued)

OTHER PUBLICATIONS

Van Walraven, Carl, and Anthony L. Weinberg. "Quality assessment of a discharge summary system." CMAJ: Canadian Medical Association Journal 152.9 (1995): 1437.*

*Primary Examiner* — Mark Holcomb
(74) *Attorney, Agent, or Firm* — Finnegan, Henderson, Farabow, Garrett & Dunner, LLP

(57) ABSTRACT

Computer-implemented systems and methods are provided for generating automated and real-time graphical user interfaces. A computerized system may include at least one processor configure to perform operations including receiving real-time status information with a identifier, loading a milestone plan including a set of milestone tasks and an initial estimated discharge time period associated with the set of milestone tasks, determining whether the real-time status information indicates completion of the milestone task, updating the milestone plan based on the real-time status information to indicate completion of the milestone task and include one or more remaining milestone tasks, automatically generating information reflecting a graphical representation of the completed milestone task and the one or more remaining milestone tasks, automatically calculating a revised estimated discharge time, and providing the generated interface update information and the revised estimated discharge time for output on the station display.

22 Claims, 18 Drawing Sheets

| BED ▲ | NAME | LC | ST | ISO TYPE | 🛏 🛏 ♿ | NURSE | ATTENDING PHYS | LOS |
|---|---|---|---|---|---|---|---|---|
| ☐ 30101 | | | | | | JA | | |
| 30201 | BLOCKED | | | | | JA | | |
| ☐ 30301 | GANT, TONI | ⊖ | C | Droplet | 🛏 ☐ ♿ | MH | AhmR | 2.2 |
| ☐ 30401 | | | | | | MH | | |
| ☐ 30501 Ⓢ | GEORGE, JENNIFER | ⊖ | D | Airborne | 🛏 ○ ☐ | JA | AbeT | 5.2 |
| ☐ 30601 | | | | | | MH | | |
| ☐ 30701 Ⓢ | | | | | | JA | | |
| ☐ 31901 | GREEN, JAMI | ⊖ | C | Contact | 🛏 ☐ ☐ | JA | AraA | 4.2 |
| ☐ 32001 Ⓢ | GRIZZARD, MARY | ⊖ | H | Arcobacter | 🛏 ☐ ☐ | MH | AndR | 0.2 |
| ☐ 32101 | GUTSHALL, JAIME | ♡ | C | Droplet | 🛏 ☐ ☐ | JA | AndJ | 10.2 |
| ☐ 32201 | | | | | | JA | | |
| ☐ (32301) | RESERVED | | | | | MH | | |
| ☐ | HAYNES, JODI | ⊕ | H | Arcobacter | 🛏 ☐ ☐ | MH | CalC | 10.2 |
| ☐ 32401 | HOBT-BINGHAM, TERESA | | C | Arcobacter | 🛏 ☐ ♿ | JA | VilV | 1.7 |
| ☐ 32501 | HUFF, EMILY | ⊕ | H | Arcobacter | 🛏 ☐ ☐ | JA | CatJ | 2.5 |
| ☐ 32601 | KEY, KRISTY | ♡ | T- | Arcobacter | 🛏 ☐ ♿ | MH | AboB | 7.6 |

600 / 610 / 615 / 630 / 635 / 640 / 645 / 650

Related U.S. Application Data

(60) Provisional application No. 62/084,360, filed on Nov. 25, 2014, provisional application No. 62/208,533, filed on Aug. 21, 2015.

(56) References Cited

U.S. PATENT DOCUMENTS

| | | |
|---|---|---|
| 2003/0074222 A1 | 4/2003 | Rosow et al. |
| 2005/0071188 A1 | 3/2005 | Thuerk |
| 2005/0215867 A1* | 9/2005 | Grigsby ............... G06F 19/327 600/300 |
| 2007/0143143 A1* | 6/2007 | Villasenor ............ G06F 19/327 705/2 |
| 2007/0150307 A1* | 6/2007 | Lancaster ............ G06F 19/327 705/2 |
| 2007/0239484 A1 | 10/2007 | Arond et al. |
| 2009/0025086 A1 | 1/2009 | Fujita et al. |
| 2011/0071851 A1* | 3/2011 | Alden ................... G06F 19/327 705/3 |
| 2011/0208534 A1* | 8/2011 | Liotta ................... G06F 19/327 705/2 |
| 2013/0297331 A1* | 11/2013 | Zuehlsdorff ........... G06Q 40/08 705/2 |
| 2013/0297350 A1 | 11/2013 | Gross et al. |
| 2013/0325515 A1* | 12/2013 | Nikolova-Simons ........................ G06F 19/327 705/3 |
| 2014/0108034 A1 | 4/2014 | Akbay et al. |
| 2015/0088536 A1* | 3/2015 | Thelen ................ G06F 19/3456 705/2 |

\* cited by examiner

| BED ▲ | NAME | LC | ST | ISO TYPE | ⊕▽ | & | NURSE | ATTENDING PHYS | LOS |
|---|---|---|---|---|---|---|---|---|---|
| ☐ 30101 | | | | | | | | | |
| 30201 | *BLOCKED* | | | | | | JA | | |
| ☐ 30301 | GANT, TONI | ⊕ | C | Droplet | ⊕ ☐ | & | JA | AhmR | 2.2 |
| ☐ 30401 | | ⊕ | D | Airborne | ⊕ ○ | | MH | | |
| ☐ 30501 Ⓢ | GEORGE, JENNIFER | | | | | | MH | AbeT | 5.2 |
| ☐ 30601 | | | | | | | JA | | |
| ☐ 30701 Ⓢ | GREEN, JAMI | ⊕ | C | Contact | ⊕ ⌂ | | MH | | |
| ☐ 31901 | GRIZZARD, MARY | ⊕ | H | Arcobacter | ⊕ ☐ | | JA | AraA | 4.2 |
| ☐ 32001 Ⓢ | GUTSHALL, JAIME | ◇ | C | Droplet | ⊕ ☐ | | MH | AndR | 0.2 |
| ☐ 32101 | RESERVED | | | | | | JA | AndJ | 10.2 |
| ☐ 32201 | HAYNES, JODI | ⊕ | H | Arcobacter | ⊕ ☐ | | JA | | |
| ☐ [32301] | HOBT-BINGHAM, TERESA | | C | Arcobacter | ⊕ ☐ | & | MH | CalC | 10.2 |
| ☐ 32401 | HUFF, EMILY | ⊕ | H | Arcobacter | ⊕ ☐ | | JA | VilV | 1.7 |
| ☐ 32501 | KEY, KRISTY | ◇ | T- | Arcobacter | ⊕ ☐ | & | JA | CatJ | 2.5 |
| ☐ 32601 | | | | | | | MH | AboB | 7.6 |

FIG. 6A

| NURSE | ASSISTANT | CASE MANAGER | | | | CURRENT LOC |
|---|---|---|---|---|---|---|
| June (4417) | Linda (1119) | Lacy (4412) | | | | H.820A |
| June (4417) | Linda (1119) | Lacy (4412) | | | | H.820B |
| June (4417) | Linda (1119) | Lacy (4412) | | | | H.821A |
| Larry (1115) | Linda (1119) | Lacy (4412) | | | | H.821B |
| Larry (1115) | Linda (1119) | Lacy (4412) | | | | H.822B |
| Larry (1115) | Linda (1119) | Lacy (4412) | | | | H.823A |
| Marie (1131) | Linda (1119) | Lacy (4412) | | | | H.823B |

FIG. 6C

Staff Assignment: H.MED2

Staff List

Search Staff List 5 of 5 Selected▼

| Name (Alias) | Phone Ext. |
|---|---|
| ⑤ June (L., June) | 4417 |
| ⑧ Lacy (B., Lacy) | 4412 |
| ④ Larry (N., Larry) | 1115 |
| ⑬ Linda (H., Linda) | 1119 |
| ④ Marie (C., Marie) | 1131 |

| Shift 1 | Shift 2 |
|---|---|
| 07:00 – 19:00 | 19:00 – 07:00 |

| Bed | Patient Information | Nurse | | Assistant | | Case Manager | |
|---|---|---|---|---|---|---|---|
| MEDICINE 2 RM H.820 BED A | Smith, G<br>C-Diff<br>IH 34 | June | 07:00 – 19:00 | Linda | 07:00 – 19:00 | Lacy | 07:00 – 19:00 |
| MEDICINE 2 RM H.820 BED B | Jones, M<br>None<br>IH 48 | June | 07:00 – 19:00 | Linda | 07:00 – 19:00 | Lacy | 07:00 – 19:00 |
| MEDICINE 2 RM H.821 BED A | White, L<br>IH 93 | June | 07:00 – 19:00 | Linda | 07:00 – 19:00 | Lacy | 07:00 – 19:00 |
| MEDICINE 2 RM H.821 BED B | Mayer, V<br>None<br>IH 83 | Larry | 07:00 – 19:00 | Linda | 07:00 – 19:00 | Lacy | 07:00 – 19:00 |
| MEDICINE 2 RM H.822 BED A | | Larry | 07:00 – 19:00 | Linda | 07:00 – 19:00 | Lacy | 07:00 – 19:00 |
| MEDICINE 2 RM H.822 BED B | Cerruli, E<br>None<br>IH 60 | Larry | 07:00 – 19:00 | Linda | 07:00 – 19:00 | Lacy | 07:00 – 19:00 |
| MEDICINE 2 RM H.823 BED A | Cellery, C<br>None<br>IH 93 | Larry | 07:00 – 19:00 | Linda | 07:00 – 19:00 | Lacy | 07:00 – 19:00 |

| Complete | > |
|---|---|

Patient:
Test 1, OutPatient

DOB:
5/5/1955

Isolation:
-

From:
PA1 ROOM 1104 BED 3

To:
N61 6C01 BED 2

Mode of Travel
Wheelchair

| Roundtrip | > |
|---|---|
| Equipment Return | > |
| Delay job | > |
| Cancel job | > |
| Request assist | > |

FIG. 6G

| Staff Assignment: H.MED2 | | | | | | |
|---|---|---|---|---|---|---|
| Staff List | | | Shift 1 | Shift 2 | | |
| Search Staff List | | | 07:00 – 19:00 | 19:00 – 07:00 | | |
| 5 of 5 Selected ▾ | | | | | | |
| Name (Alias) | Phone Ext. | Bed | Patient information | Nurse | Assistant | Case Manager |
| ③ June (L., June) | 19:00 21:00 4417 | MEDICINE 2 RM H.820 BED A | ● Smith, G C-Diff | IH 34 | June 07:00 – 19:00 | |
| Lacy (B., Lacy) | 4412 | MEDICINE 2 RM H.820 BED B | ● Jones, M - None | IH 48 | June 07:00 – 19:00 | |
| Larry (N., Larry) | 1115 | MEDICINE 2 RM H.821 BED A | ● White, L | IH 93 | June 07:00 – 19:00 ☒ | |
| ⑤ Linda (H., Linda) | 1119 | MEDICINE 2 RM H.821 BED B | Mayer, V None | IH 83 | | |
| Marie (C., Marie) | 1131 | MEDICINE 2 RM H.822 BED A | | | | |
| | | MEDICINE 2 RM H.822 BED B | Cerruti, E None | IH 60 | | |

FIG. 8B

Staff History Report Generator

Please enter one or more of the following:

- Patient Name: Smith, Patricia — 910
- Patient ID: — 920
- Start Date: 07/11/2014 — 930
- End Date: 07/14/2014 — 940
- Unit: — 950
- Caregiver Name: — 960

[Exit] [Clear] [Generate]
970

SYSTEMS AND METHODS FOR GENERATING AUTOMATED REAL-TIME GRAPHICAL USER INTERFACES

CROSS REFERENCE TO RELATED APPLICATIONS

This application is a continuation-in-part of U.S. patent application Ser. No. 14/950,463, filed Nov. 24, 2015, which claims the benefit of priority based on U.S. Provisional Patent Application No. 62/084,360 filed on Nov. 25, 2014, and U.S. Provisional Patent No. 62/208,533 filed on Aug. 21, 2015, the entire disclosures of which are incorporated by reference.

TECHNICAL FIELD

The present disclosure is directed to the technical field of centralized network communications and data distribution. More particularly, disclosed embodiments are directed to centralized server-based communication systems for generating automated and real-time graphical user interfaces for distribution to networked terminals.

BACKGROUND

Modern hospitals intake and discharge hundreds of patients in individual facilities every day. When patients are nearing the completion of their treatment plan, they begin a discharge process which often requires the coordination and communication of multiple departments in the hospital. In many situations, the patient must be transported to various areas of the hospital, multiple individuals must visit the patient, and sometimes the patient must meet with multiple physicians located in different hospital units or facilities. Accomplishing these tasks requires frequent and constant exchange of data and information throughout the hospital and between multiple hospitals.

Traditional communication techniques for event detection and communication during the discharge process are based upon outdated communication technologies, resulting in overloaded systems that are slow, error-prone, and do not provide facility-wide communication using a centralized system. Indeed, traditional techniques usually rely upon multiple disparate systems, which may not integrate and exchange information. Some traditional techniques involve manual reporting of an event and/or manual requests for transportation, usually through phone calls between individuals in the facility. At the scale of modern hospital operations, traditional systems usually result in overloaded telephone lines, missed requests.

In view of the technical deficiencies of current systems discussed above, there is a need for improved systems and methods centralized real-time event detection and communication.

SUMMARY

Disclosed embodiments relate to a computerized system for generating and distributing automated real-time graphical user interfaces to reflect the processed data corresponding to detected events in a facility. In some embodiments the events can include the creation or completion of milestones in a discharge protocol for a given patient. In some embodiments, the system may comprise at least one processor configured to receive a patient bed assignment request. The patient bed assignment request may include a patient identifier and a bed identifier. The one or more processors may receive, based on a query made in response to the received patient bed assignment request, patient medical treatment data corresponding to the patient identifier. The one or more processors may also format information from the patient medical treatment data for display.

In some embodiments, improved systems and methods are provided for automated caregiver assignment. The automated caregiver assignment function of such an embodiment integrates a patient's nurse assignment from 3rd-party systems (such as one or more nurse call and nurse assignment systems) directly into the system to generate a comprehensive and robust graphical user interface that can provide large quantities of information quickly and efficiently to users in a demanding and fast-paced environment. This integration eliminates data entry in separate systems and improves coordination of care, saving time and minimizing errors associated with manual entry.

Consistent with the present embodiments, a computerized system is disclosed. The system may include at least one networked processor, and a storage medium comprising instructions. When executed, the instructions may cause the at least one networked processor to automatically generate an interactive graphical user interface for a station display in communication with the at least one networked processor, by receiving, via a network, real-time status information with a patient identifier, loading a milestone plan corresponding to the patient identifier, the milestone plan including a predetermined set of milestone tasks and an initial estimated discharge time period associated with the set of milestone tasks, responsive to determining that the real-time status information corresponds to one of the milestone tasks, determining whether the real-time status information indicates completion of the milestone task, updating the milestone plan based on the real-time status information to indicate completion of the milestone task and include one or more remaining milestone tasks, automatically generating interface update information reflecting a graphical representation of the completed milestone task and the one or more remaining milestone tasks updated milestone plan, automatically calculating a revised estimated discharge time based on the initial estimated discharge time period, a current time, and a time period associated with the completed milestone task or the one or more remaining milestone tasks, and providing the generated interface update information and the revised estimated discharge time for output on the station display.

Consistent with the present embodiments, a system is disclosed for generating a graphical user interface of real-time patient information. The system may include at least one processor and a storage medium. The storage medium may include instructions that, when executed, cause the at least one processor to automatically update a nursing station display. The update may include receiving, at the at least one processor from a network, a patient bed assignment request, the patient bed assignment request including a patient identifier and a bed identifier. The update may also include receiving, at the at least one processor from the network, based on a query made in response to the received patient bed assignment request, a patient medical treatment data corresponding to the patient identifier. Additionally, the update may include formatting information from the patient medical treatment data for display. The update may further include transmitting display instructions to a nursing station user interface based on the formatted information.

Consistent with the present embodiments, a computerized method for automatic and real-time interactive graphical user interface generation is disclosed. The method may comprise receiving, by at least one networked processor via a network, real-time status information with a patient identifier, loading a milestone plan corresponding to the patient identifier, the milestone plan including a predetermined set of milestone tasks and an initial estimated discharge time period associated with the set of milestone tasks, responsive to determining that the real-time status information corresponds to one of the milestone tasks, determining whether the real-time status information indicates completion of the milestone task, updating the milestone plan based on the real-time status information to indicate completion of the milestone task and include one or more remaining milestone tasks, automatically generating interface update information reflecting a graphical representation of the completed milestone task and the one or more remaining milestone tasks updated milestone plan, automatically calculating a revised estimated discharge time based on the initial estimated discharge time period, a current time, and a time period associated with the completed milestone task or the one or more remaining milestone tasks, and providing the generated interface update information and the revised estimated discharge time for output on the station display.

Consistent with the present embodiments, a method is disclosed for generating a graphical user interface of real-time patient data. The method may include receiving, at the at least one processor from a network, a patient bed assignment request, the patient bed assignment request including a patient identifier and a bed identifier. The method may additionally include receiving, at the at least one processor from the network, based on a query made in response to the received patient bed assignment request, a patient medical treatment data corresponding to the patient identifier. The method may also include formatting information from the patient medical treatment data for display. The method may include transmitting display instructions to a nursing station user interface based on the formatted information.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIGS. 6A-6G are illustrations of example graphical user interfaces consistent with embodiments of the present disclosure.

FIG. 8B illustrates an example caregiver history view graphical user interface, consistent with embodiments of the present disclosure.

FIGS. 9 and 10 are illustrations of examples of a staff history report generator interface, consistent with embodiments of the present disclosure.

DETAILED DESCRIPTION OF EXEMPLARY EMBODIMENTS

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
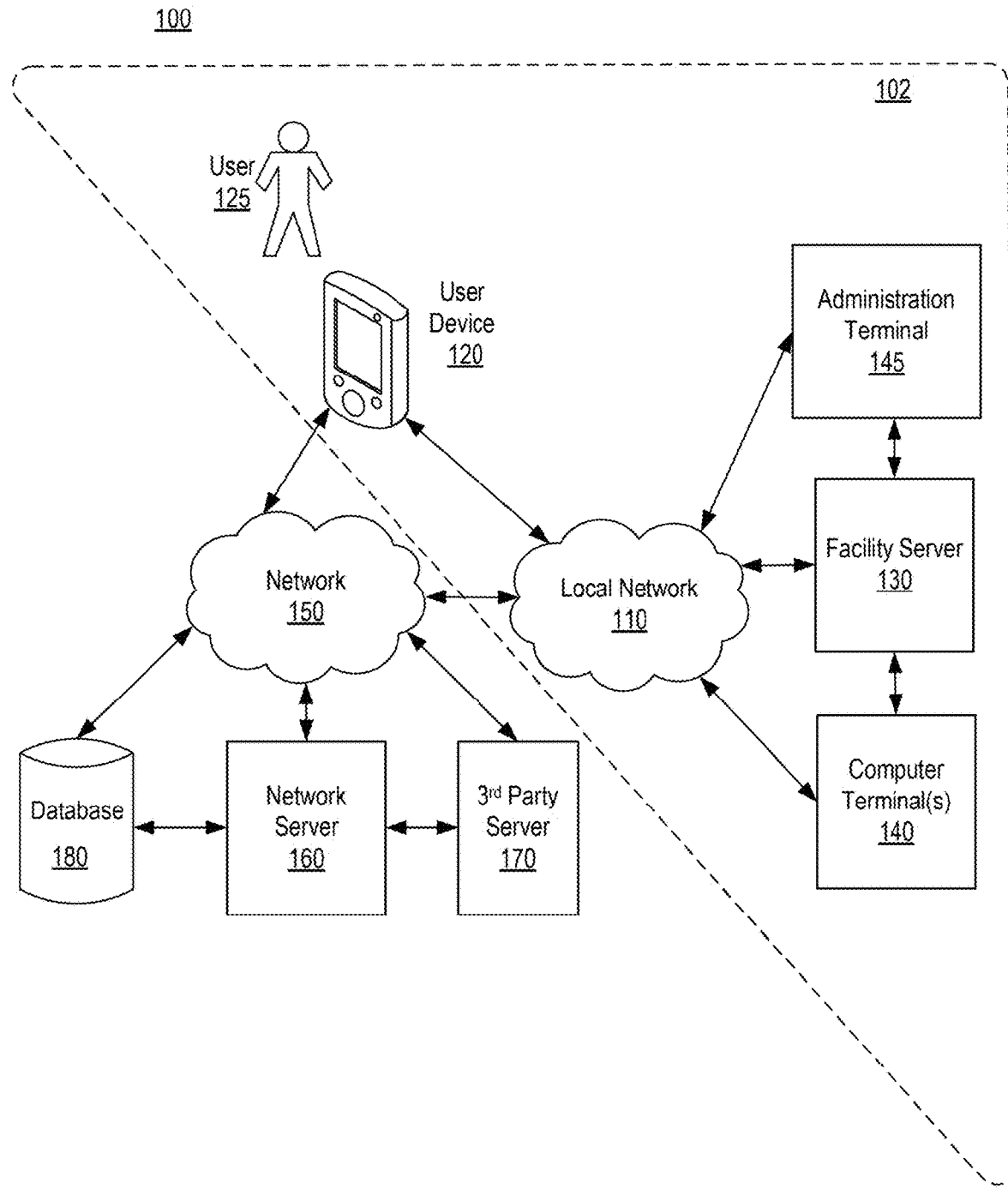
FIG. 1 depicts an example of a system environment for tracking patients within an organization, consistent with embodiments of the present disclosure.

FIG. 1 shows a diagram of a workflow automation and management system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, workflow automation and management system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a medical facility such as a hospital or office building (i.e. as facility system 102) while network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, touch screen monitor, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include computer system or device associated with a user 125 that manages or oversees a portion of facility system 102. For example, administrator terminal 145 may comprise a computer system located at a head nurse station, a housekeeping manager's office, or any other department manager's office or station.

User 125 may be an employee in a workplace environment such as a nurse, a technician, supervisor, manager, support personnel, or a dispatcher. User 125 may operate computer terminal 140, user device 120, and/or another computer (not shown) to interact with system 100. System 100 may include multiple types of users such as, for example, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™' Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, Third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
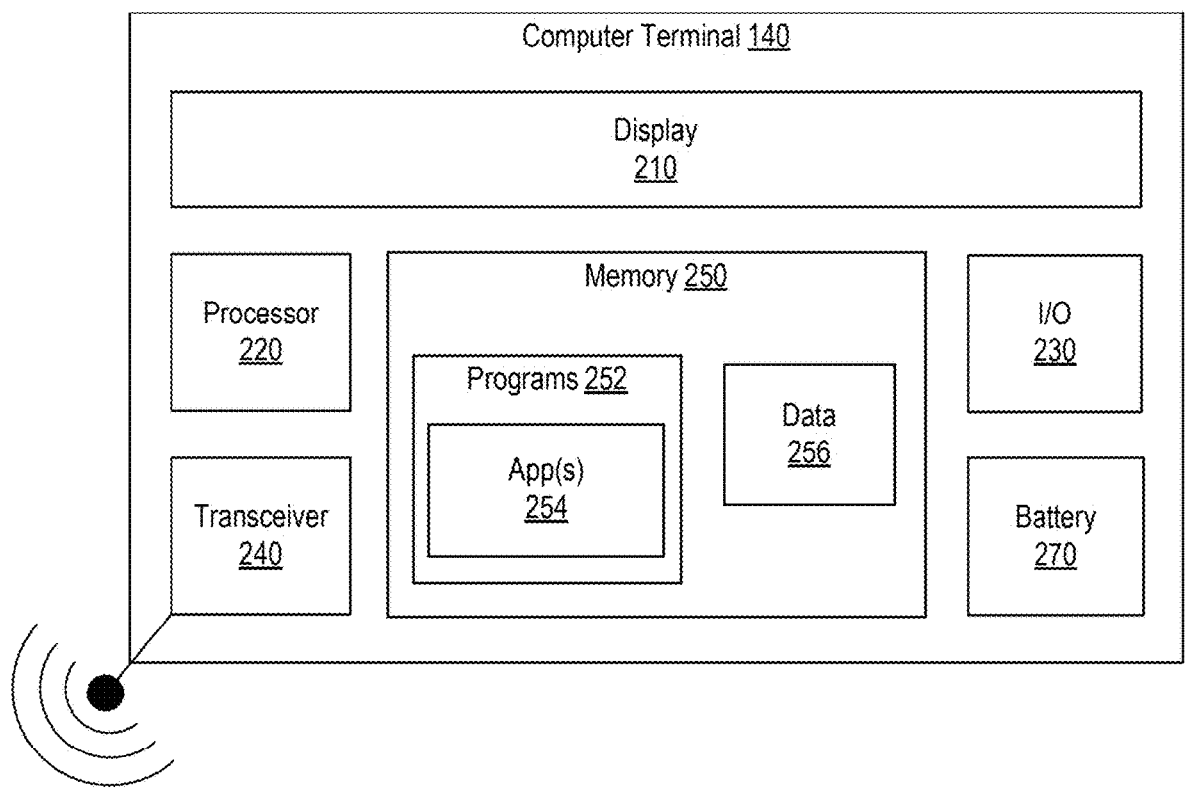
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and ZigBee. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for prioritizing and assigning tasks to one or more employees.

Program(s) 252 may include operating systems (not shown) that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a task administration app, which when executed causes computer terminal 140 to perform processes related to managing, prioritizing, and scheduling multiple pending tasks. For example, app(s) 254 may configure computer terminal 140 to perform operations including receiving input of task information, displaying pending tasks, monitoring task status, assigning tasks to employees, and displaying employee task assignments.

Figure 3:
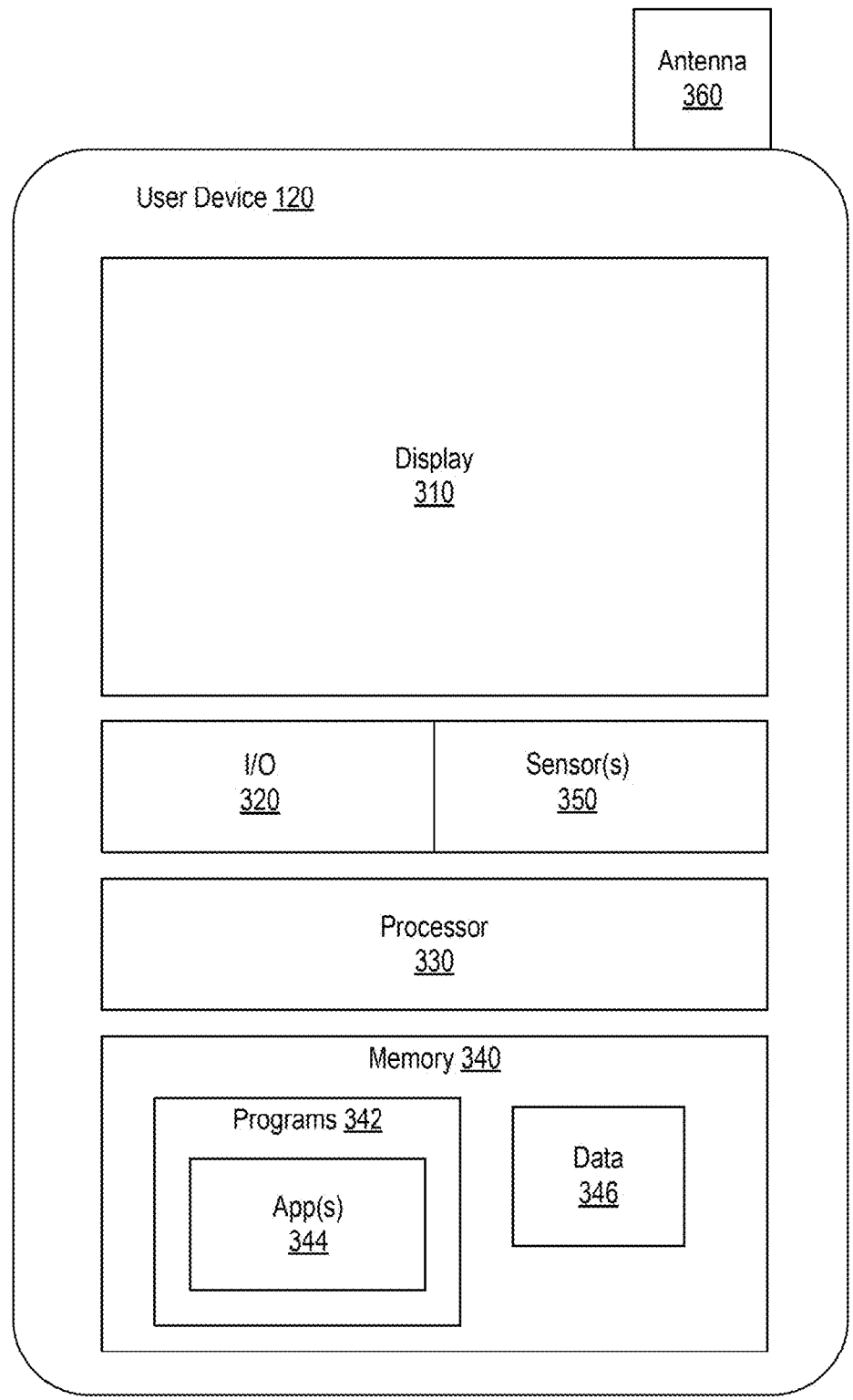
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
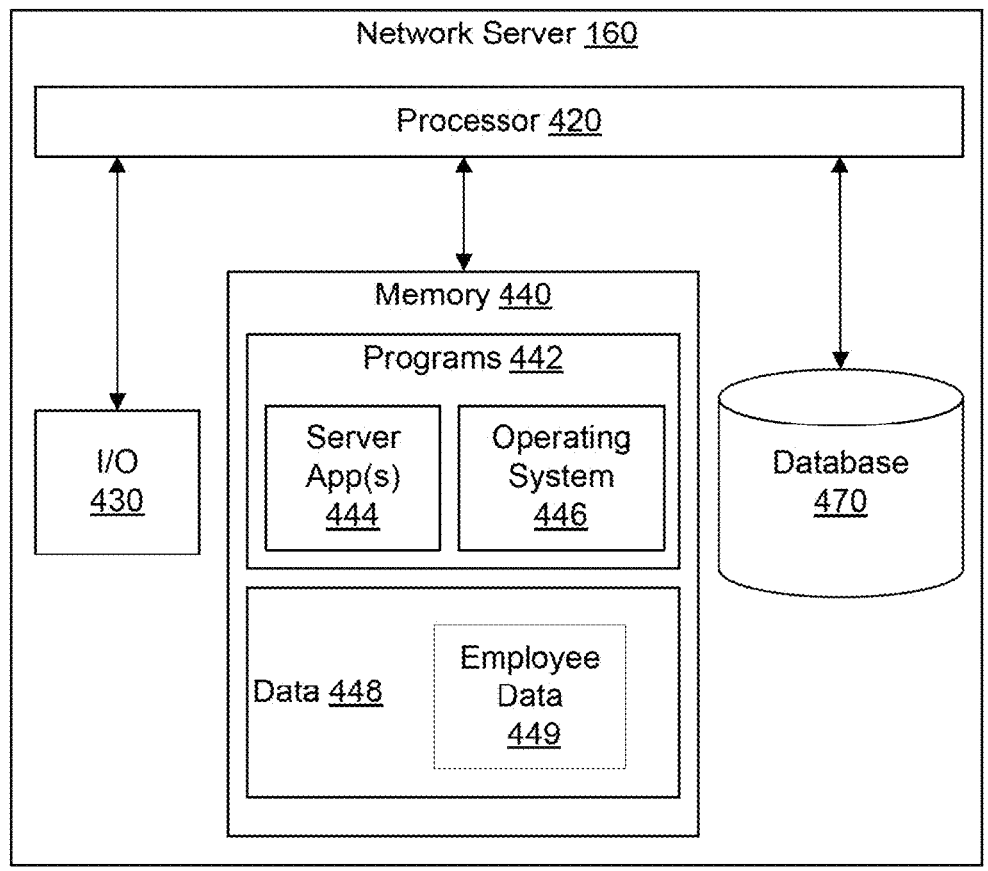
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure™ or Amazon Web Services™. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as a request for an equipment item to be transported between facilities. Additionally, network server 160 may collect data from multiple facilities to evaluate performance times in different facilities, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448

(including employee data 449), and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to tracking patient statuses such as receiving patient bed requests, receiving patient attributes and conditions, receiving staff schedules and staff skills, receiving one or more hospital rules and legal restrictions, analyzing received data using one or more rule sets, computer models, or other processing logic, generating data associated with one or more graphical user interfaces, and updating the graphical user interfaces in real-time based on new data or changes in the analysis results.

In some embodiments, memory 440 may store data 448 including data associated with patients, staff, tasks, assets such as hospital beds, assignment and graphical user interface generation algorithms, and any other data related to the disclosed embodiments. For example, data 448 may include one or more entries including employee data 449 (e.g., identifications of staff, their skill sets, their schedules and availability, staff assignment history), patient medical records, patient assignment history, data associated with patient conditions, patient bed assignments, bed availability, bed locations, bed attributes, hospital rules, legal and restrictions and regulations. Data 448 may also include the current location of the patient, the status of each of the patient physician orders (e.g., lab orders, radiology orders), bed assignment priorities, milestones (e.g., discharge and transfer milestones), transport request status, patient hand-off during shift change, continuity of care data for resource assignments, and custom patient attributes. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, Share Point databases, Oracle™ databases, Sybase™ databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, Share Point databases, Oracle™ databases, Sybase™ databases, or other relational databases. Systems and methods consistent with disclosed embodiments, however, are not limited to separate databases or even to the use of a database.

Figure 5:
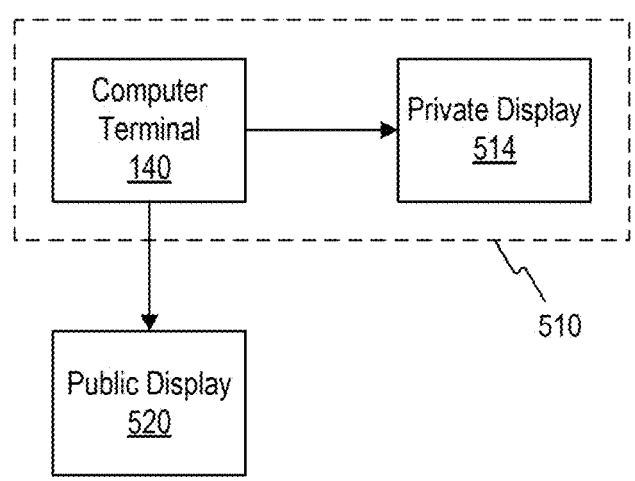
FIG. 5 depicts an example of a nursing station computing system, consistent with embodiments of the present disclosure.

FIG. 5 depicts an example of nursing unit computing system 500, consistent with certain embodiments. As shown, system 500 may include computer terminal 140 connected to private display 514 and public display 520.

In some embodiments, private display 514 may include a computer monitor (e.g., LCD display) that is viewable only by nursing staff. For example, private display be located and oriented outside of public view as part of nurse workstation 510. Privacy laws and health regulations may prohibit the open display of certain patient information. For example, the Health Insurance Portability and Accountability Act (HIPAA) may prohibit the medical facility from publicly displaying a particular condition or diagnosis of a patient, or the patient's identification. However, nursing staff may need to reference this heath information to provide care for patients. Private display 514 may be configured to allow medical facility staff, but not visitors (e.g., the public), to view patient information. Private display 514 may be a monitor placed behind an access-restricted area, such as behind a personnel counter or in an access-controlled room. In some embodiments, private display 514 may include a privacy screen to prevent passersby from viewing information displayed on private display 514. In other embodiments, additional physical and computer features may be used to prevent the public (e.g., non-staff, visitors, etc.) from viewing private display 514, such as requiring nursing staff to present authentication credentials to activate the display (e.g., user identifier, password, RFID badge, and/or fingerprint scan). Private display may use facial recognition to determine whether the viewer is a member of hospital staff prior to displaying private screen information.

In some embodiments, public display 520 may include a monitor that is placed in public view. For example, public display 520 may include a large display that is placed in a corridor of a nursing unit or a hallway of a hospital. Public display 520 may be a large, wall-mounted LCD display. Other display hardware may be used in public display 520, such as a projector and white screen, such as a wall of a hospital hallway, for rear- or front-projection.

In some embodiments, computer terminal 140 may provide output for private display 514 and public display 520. Computer terminal 140 may provide similar information for display on private display 514 and public display 520. However, because public display 520 is publicly viewable, computer terminal 140 may not include sensitive patient information in output for public display 520. As further discussed with reference to FIG. 7, computer terminal 140 may perform processes to identify sensitive information (e.g., based on HIPAA rules, government regulations, and/or hospital policies) and modify the output for public display 520 to not display sensitive information. For example, public display 520 may not include full patient names or diagnosis information. System 500 may allow hospital administrators to configure information shown on public display 520 in a way that protects private health information, such as using discrete symbols or codes that are only known by trained hospital personnel.

Figure 6B:
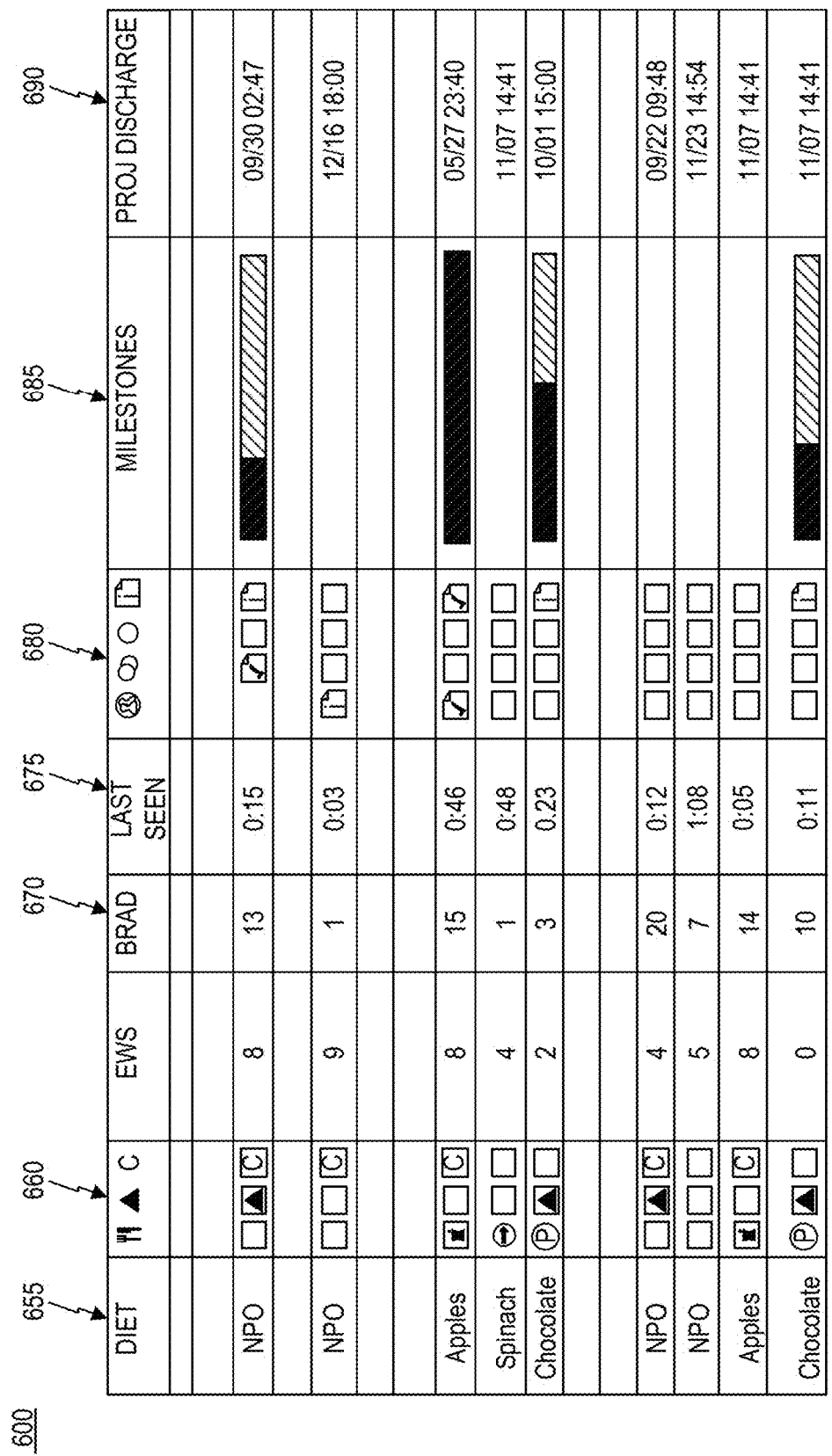

FIGS. 6A and 6B are illustrations of an example of patient tracking interface 600. Interface 600 is described herein as being provided by computer terminal 140 for display on private display 514 and public display 520. However, in some embodiments, user device 120, facility server 130, network server 160, third-party server 170, and/or database 180 may perform functions to facilitate the generation and display of interface 600.

In some embodiments, interface 600 may present patient information in an organized format such as a table. For example, interface 600 may include a plurality of cells organized in a grid. The cells may be organized in rows corresponding to bed identifiers (e.g., numbers). Interface 600 may include a list of bed identifiers 610 in a column. Interface 600 may include additional columns to display attributes corresponding to a particular bed.

In some embodiments, bed identifiers 610 may be a code corresponding to a space in a room. For example, bed identifiers 610 may be alphanumeric values that correspond to permanent room locations. While a hospital may reassign beds to different nursing units, the bed identifier may always refer to the same physical space in a particular room, regardless of what bed furniture may be present in the room. In other embodiments, bed identifiers 610 may refer to a particular physical bed that may be moved from room to room. An additional room identifier (not shown) may designate a physical space in a room. For example, a patient may be moved from one room to another using a rolling bed. In this example, computer terminal 140 may receive data indicating that the patient has changed to a new room identifier, but the bed identifier remains the same. In some embodiments, bed identifiers 610 may correspond to bedside computing terminals. The terminals may belong to bed furniture or a physical room location. For example, when a bedside computing terminal is mounted on a bed, the preferred identifier (e.g., bed identifiers 610) may correspond to the bed furniture. When a bedside computing terminal is mounted on a wall of a hospital room, the preferred identifier (e.g., bed identifiers 610) may correspond to the physical room location.

In some embodiments, bed identifiers 610 may include annotations. Computer terminal 140 may alter the style of the font used to present the text of bed identifiers 610 to visually differentiate the text of bed identifiers 610. For example, computer terminal 140 may change the text of bed identifiers 610 to be bolded, italicized, enlarged, minimized, colored, and/or underlined to indicate a particular status of the corresponding bed. As illustrated in FIG. 6A, computer terminal 140 has bolded "BED 30201" that may indicate that the bed has been blocked from use. In other examples, computer terminal 140 may add additional characters to the bed identifier text. For example, as shown in FIG. 6A, a bed identifier is surrounded by square brackets ("[32301]") which may indicate that the bed has been reserved. In still other examples, symbols or icons may accompany bed identifiers 610. In some embodiments, the bed status may be input by a nurse or hospital employee via one or more computer terminal 140, or via mobile device 120, and processed by facility server and/or network server 160. In some embodiments, one or more sensor attached to a bed may provide facility server 130 or network server 160 with real-time status information about a particular bed, such as an occupancy status based on a detected weight load on the bed, a movement status based on detected motion from an accelerometer, or location based on a location sensor. Interface 600 may update in real-time as new information is received and processed.

Interface 600 may include a list of patient names 615. In some embodiments, computer terminal 140 may receive a patient name for a particular bed. For example, network server 160 may forward a bed assignment request to computer terminal 140. Computer terminal 140 and/or network server 130 may automatically associate a patient name with a bed number in response to an assignment request. For example, network server 160 may automatically select a bed identifier for a bed that matches needs and settings of a particular patient, based on a patient record stored in database 180 or 470. Computer terminal 140 may update interface 600 to include the new patient name from the assignment request in patient names 615 in the row corresponding to the bed indicated in the assignment request for the patient.

Patient names 615 list names of patients. In some embodiments, patient names 615 may be legal names of patients. For example, patient names 615 may include "John Smith" or any of the names shown in FIG. 6A. In other embodiments, patient names may include abbreviated names, initials, aliases, and/or nicknames that can distinguish between patients divulging their actual name. For example, patient names may include "J. Smith," "J.E.S.," "Johnny S.," or "Blonde John," respectively, for a patient named John Eli Smith. In additional embodiments, patient names may include additional combinations of patient identifiers, such as numbers, letters, and/or symbols.

In some embodiments, the column for patient names 615 may include bed status identifiers when there is no patient assigned to the bed to convey the bed status. Computer terminal 140 may receive bed information indicating that a bed is not available for assignment to a patient. For example, computer terminal 140 may receive a patient placement request in advance of a patient arrival to the bed. When computer terminal 140 receives instructions indicating that a bed is planned to be occupied by an incoming patient, but the patient has not yet arrived to the nursing unit, computer terminal 140 may update patient names 615 in interface 600 to indicate that the bed is "reserved." In some embodiments, network server 160 may automatically indicate that a bed is reserved, based on information received from one or more other systems. For example, a patient may be exiting an operating room and need a bed assignment. If data associated with an operating room includes a patient identifier that is not currently assigned to a bed, then network server 160 may automatically determine which available bed is suitable for the patient by comparing patient attributes and bed attributes, and network server 160 may automatically reserve a bed for the patient. In another example, a bed or room may experience operational defects and not be suitable to host a patient. In such an example, computer terminal 140 may receive input from a hospital staff member indicating that the bed is unavailable or, as shown in FIG. 6A, "blocked." The column for patient names 615 may include additional status indicators to convey pertinent information about the corresponding bed or room, such as when the bed is not assigned to a patient and there is no name to display. For example, patient names 615 may indicate that a particular bed "needs changing" or is "clean" or "dirty." In some embodiments, interface 600 may prioritize the display of a patient identifier over a bed status indicator when a bed is occupied. For example, when a bed "requires cleaning" and a patient is occupying the bed, interface 600 may display the patient name, rather than the bed status indicator. In an alternative embodiment, interface 600 may alternate the display of the bed status indicator and the patient names in the column for patient names 615.

Interface 600 may display patient status information. Patient status information may convey data about a patient's current state of health or data about a patient's current hospital visit. Patient status information may be calculated locally by computer terminal 140, received by computer terminal 140 from database 180, and/or received by computer terminal 140 as local peripheral input.

In some embodiments, patient status information may include isolation types 630. Computer terminal 140 may receive data from database 180 (e.g., electronic health records) indicating that a patient's illness may require him or her to be isolated from particular forms of contact with other individuals. For example, when a patient is contagious, the patient may require airborne isolation to prevent a virus from spreading to other patients.

Isolation types 630 shown by user interface 600 may inform nurse and doctor patient interaction protocols. For example, computer terminal 140 may receive hospital or health board protocols for interacting with patients in airborne isolation. Computer terminal 140 may provide an announcement indication to a bedside terminal, such as a graphical room station (GRS), in the corresponding patient's room, providing instructions on how to safely interact with the patient, such as providing graphical instructions on the display of the bedside terminal instructing the nurse to use a facemask or nitrile gloves when interacting with a patient. As shown in FIG. 6A, example isolation types may include "droplet," "airborne," "contact," and "acrobacter." Additional isolation types may be known in the field and used to convey patient interaction restrictions.

In some embodiments, patient status information may include length of stay (LOS) data 650. Computer terminal 140 may record the timestamp that the patient enters a nursing unit or hospital. Computer terminal 140 may calculate the difference between the current date and time and the date and time the patient entered the nursing unit as LOS data 650. Computer terminal 140 may update interface 600 with LOS data 650, indicating that a user has stayed within the hospital for 2.2 days, for example. In other embodiments, LOS data 650 may use alternative units and formats, such as hours or "2 days, 3 hours." Other display formats and units may be used commensurate with this disclosure. In some embodiments, computer terminal 140 may cause interface 600 to display one or more symbols with LOS data 650, or change an appearance of LOS data 650 based on the determined length. For example, computer terminal 140 may compare LOS data 650 to one or more thresholds predetermined by the hospital or determined dynamically based on one or more rules associated with a condition or attribute of the patient, a capacity status of the hospital, or a policy of the hospital. Based on the comparison, computer terminal 140 may update the appearance of LOS data 650 in real time to provide an immediately-recognizable indication. For example, if a particular patient has undergone major surgery, computer terminal may determine, based on one or more stored rules, that the patient's length of stay should be 2-3 weeks. As the patient's length of stay approaches the predefined threshold, the displayed LOS data 650 may change from green to yellow. When the length exceeds the predefined threshold, the LOS data 650 may change from yellow to red, or from yellow to orange. Other color schemes and types of visual indications may be used, depending on the needs and preferences of the hospital. In some embodiments, computer terminal 140 may receive one or more modifications to the length of stay thresholds from an individual such as a nurse, doctor, or hospital administrator, to vary the depicted information for each patient, for units of patients, or for the entire hospital.

In some embodiments, patient status information may include diet data 655. Computer terminal 140 may receive doctor provided diet requirements from network server 160. For example, patient records may indicate that, as part of the patient's treatment, the patient should eat spinach, drink clear liquids only, or have low sodium meals. Diet data may also indicate that the patient is diabetic or has specific food allergies.

In some embodiments, patient status information may include patient attribute icons 660. Computer terminal 140 may receive patient attribute information from database 180, network server 160, third-party server 170, and/or local input. For example, database 180 may transmit a patient record to computer terminal 140 indicating that the patient is a fall risk. Computer terminal 140 may aggregate patient information, identify corresponding symbols for the information, and provide instructions to update interface 600 with the corresponding symbols. For example, computer terminal 140 may reference a database of common patient attributes and standardized symbols to determine that a triangle is the symbol indicating that the patient is a fall risk. Computer terminal 140 may update interface 600 to display a triangle for patient attribute icons 660 in the row for the particular patient.

In some embodiments, patient status information may include quantitative evaluations of a patient's health condition. For example, as shown in FIG. 6B, user interface may include Braden scores 670. Computer terminal 140 may receive input and calculate evaluation scores for patients. For example, computer terminal may include prompts to solicit information from caretakers using input devices (e.g., touch screen and/or keyboard). In other examples, computer terminal 140 may receive lab results for a patient. Computer terminal 140 may calculate quantitative scores to provide patient status evaluations from nurse input data or laboratory results data.

In some embodiments, patient status information may include last seen data 675. Computer terminal 140 may calculate the time that has elapsed since the patient was last seen by a caretaker. For example, computer terminal 140 may receive data from sensors in patient rooms indicating when caretakers entered the room. Example sensors may include RFID sensors that read RFID badges of caretakers. Other example sensors may include cameras, infrared proximity sensors, or tactile door sensors that may provide data indicating entry to a given hospital room. The sensors may transmit timestamps to computer terminal 140 indicating the time visits occurred and, when sensor capabilities permit, who entered the room. Computer terminal may calculate a time difference between the current time and the latest visit timestamp to determine the time elapsed since the patient was last seen by a hospital staff member. Computer terminal 140 may transmit instructions to interface 600 to update last seen data 675. Last seen data 675 may also include the type of visitor (e.g., physician, nurse, non-staff) and the duration of their visit (e.g., entry and exit times), along with a narrative summarizing the visit. For example, a visit entry of last seen data 675 may indicate that Doctor William Strawberry visited patient Sue Thompson from 10:05 AM EST to 10:17 EST on Apr. 1, 2011. This example visit entry may also include a narrative stating that Doctor Strawberry discussed symptoms with patient and conveyed dietary guidelines to reduce blood pressure.

In some embodiments, interface 600 may include patient care information. In some embodiments, patient care information may include support icons 635 indicating support services for patient care. Support icons may reflect the status of third party care services for the patient. For example, computer terminal 140 may receive patient data from network server indicating that the patient has trouble moving between units for testing and treatment. Computer terminal 140 may identify support services to fulfill patient needs and interface with the corresponding third-party server 170 for the support service. Computer terminal 140 may update support icons 635 in interface 600 to provide a visual indication that the support service is available and, when requested, the status of the support service received from third-party server 170.

In some embodiments, support icons 635 may allow users to directly request support services. User interface may receive a user selection of a support icon. In response to the selection, computer terminal 140 may query third party server 170 for the service corresponding the service. For example, user interface 600 may receive a user selection of a transport support service icon. Computer terminal 140 may process the selection and initiate transport support service request by transmitting a request to third party server 170 for transport support services. Additional support icons 635 may be used to facilitate interactions with servers for managing other support services.

In some embodiments, patient care information may include nurse data 640 or attending physician data 645. Computer terminal 140 may determine staff assignment data for each patient. In some embodiments, nurse and physician assignments may be determined automatically based on one or more schedules stored in a database, or may be entered manually by a staff member Computer terminal 140 may transmit staff assignments to interface 600 to update the display. As shown in FIG. 6A, nurse data 640 identifies nurses based on their initials, and attending physician data identifies attending physicians based on their abbreviated name. Other staff identifiers may be used such as, for example, a first name, last name, full name, or initials. Additional columns may list other types of hospital staff assigned to particular patients when appropriate.

In some embodiments, patient care information may include care progress indicators 680, milestones 685, and projected discharge data 690. Interface 600 may display data indicating patient treatment progress. Computer terminal 140 may receive patient progress updates from network server 160, from mobile device 120, or from one or more sensor devices (not shown). For example, computer terminal 140 may receive an indication from user 125 via mobile device 120 that a treatment or test was completed. As another example, computer terminal 140 may receive an indication from a nurse or doctor via a system device that the patient is ready for discharge, or is not ready for discharge. As yet another example, computer terminal 140 may receive an indication from a system device the patient was successfully moved from the bed to the hospital lobby, curbside, or to a receiving family member. Computer terminal 140 may monitor the progression and compare the patient progress with a treatment plan store in database 180. The treatment plan may include goals or "milestones." When computer terminal 140 receives a progress update that corresponds to a milestone goal in the patient treatment plan, computer terminal 140 may update the corresponding one of care progress indicators 680.

In some embodiments, interface 600 may include a configurable set of discharge milestones. A predetermined checklist may be stored as a default list of discharge milestones to complete before releasing the patient. In some embodiments, the default list may include, for example, clean labs report, schedule follow-up appointment, fill prescriptions, arrange transportation, meet with social worker, and receive physician approval. In some embodiments, hospitals or nursing units may modify the checklist to include additional or fewer checklist items, based on the needs of the unit, the hospital, or the patient. In some embodiments, the hospital may further configure the checklist to include optional and mandatory items (e.g., a patient is required to have the doctor's discharge approval). In some embodiments, interface 600 may update based on data received from a third party system (e.g., third party server 170), such as when third party system 170 provides a status update for lab tests or results.

In some embodiments, system 100 may include different milestone checklists based on the patient's condition or treatment. In some embodiments, a set of rules or logic may identify the milestones associated with particular patient conditions or treatments. For example, the reason for the patient's visit, the patient diagnosis, and treatment received may be used to automatically generate a customized checklist of milestones that must be completed before the patient is ready for discharge. Interface 600 may reflect the milestones in the customized list by indicating the completion status of the milestone list. For example, a heart arrest patient may need to schedule a follow-up appointment with a cardiologist, while an orthopedics patient may require a milestone to schedule a physical therapy appointment. In some embodiments, system 100 may use one or more treatment codes to index and identify potential milestone checklists.

In some embodiments, interface 600 may indicate a percentage completion of a current milestone. Computer terminal 140 may determine that care progress updates correspond to an intermediate state of progress. Computer terminal may determine a percentage completion of an individual milestone based on the interim progress updates. For example, computer terminal 140 may receive an update from third-party server 170 indicating that an x-ray has been processed but is awaiting analysis from a radiologist. In another example, a computerized IV administration device may indicate that a patient has completed 67% of an intravenous drug dose. Computer terminal 140 may transmit a percentage milestone completion and a corresponding current milestone to interface 600 for display in milestones 685.

In some embodiments, interface 600 may display projected discharge data 690. Computer terminal 140 may calculate patient milestone progression. Based on the progression rate and treatment plan, computer terminal 140 may determine how much time is needed to complete the remaining portions of the patient's treatment plan. For example, computer terminal 140 may determine that the patient will need three additional days to complete the necessary physical therapy clinics during treatment for a stroke. Computer terminal 140 may provide the estimated discharge date to interface 600 for display in projected discharge data 690.

In another embodiment, projected discharge data 690 may correspond to an actual scheduled discharge by third party server 170. A discharge unit of a hospital may receive a discharge request from a nursing unit. The discharge unit third party server 170 may perform the necessary administrative tasks to facilitate the patient discharge. Third party server may calculate and transmit a projected discharge based on real-time discharge scheduling.

In some embodiments, projected discharge data 690 may include both estimate projections and scheduled discharges. Computer terminal 140 may utilize both calculated projections and scheduled discharge information from third party server 170. For example, interface 600 may display scheduled discharge times when available and provide estimations in all other instances.

Interface 600 may display and facilitate interaction with additional fields, including fields that are not displayed in FIGS. 6A and 6B. For example, interface 600 may include additional fields such as those as indicated in Table 1 below. Table 1 includes an exemplary list of fields, and additional fields may be included depending on the needs and capabilities of the hospital.

TABLE 1

| Column | Description |
| --- | --- |
| Accommodation | Whether the bed is private or semi-private. |
| Acuity | The measurement of intensity of care the patient requires. |
| Admit Date/Tim | Date and time that the patient was admitted. |
| Admit Source | How the patient was admitted (e.g., through the Emergency Room or through physician referral). |
| Admit Type | Why the patient was admitted (e.g., for surgery, for an emergency, or for testing). |
| Admitting Physician | Physician who ordered the patient to be admitted (e.g., the physician's alias. |
| Age | The patient's age. Additionally, a blue background may indicate a male patient. A pink background may indicate a female patient. In some embodiments, a user may tap and hold the age to see the patient's date of birth. |
| Assigned Bed Status | Status of the assigned bed (e.g., dirty). |
| Assigned Bed | Bed to which the patient has been assigned. |
| Assigned by User | User who assigned the bed to the patient. |
| Assigned Date | Date and time that the patient was assigned to the bed. |

TABLE 1-continued

| Column | Description |
| --- | --- |
| Time Assignment Timer | The number of hours and minutes between when the patient was assigned to a bed and a target time (e.g., when the patient's placement request was activated when the patient became ready to move, or another target time). |
| Assistant | The assistant for the patient or bed. For example, in a patient row, the Assistant column may show the name or alias of the assistant who is assigned to the patient for the selected unit and the current date and shift. In a bed row, the Assistant column may show the assistant who is assigned to the bed for the selected unit and the current date and shift. In some embodiments, a blank cell may indicate that an assistant is assigned to the shift, but not to a particular bed or patient. |
| Attending Physician | Physician who is responsible for the patient's care while the patient is in the hospital. |
| Attending Physician Service | The service or specialty that the attending physician provides to patients (e.g., Hematology). |
| Bed Attributes | This column may display any special bed characteristics that a patient requires (e.g., negative air flow bed, isolation, etc.). |
| Bed Delayed | The hours and minutes that a bed cleaning job for the assigned bed has been delayed. |
| Bed Size | The bed size of the patient's home location (in a patient row) or of the location shown in the Bed column (in a bed row). |
| Bed Size Requested | The bed size that was requested for the patient. |
| Bed Status Reason | In some embodiments, the system may require a reason code when changing a bed's status. For example, if a bed's status is changed to "Blocked," the system may require the assistant who blocks the bed to select a reason code (e.g., maintenance). If a reason code was selected when the bed status was changed, it may appear in this column. |
| Comments | Any notes that were entered in the Comments box on the Patient Placement/Details form or in the Comments column of a list view for this patient. |
| Current Location | The bed that the patient is currently associated with. For example, if the patient is currently in a specialty bed having a procedure, but has a different home location (bed), then the Current Location column may display the specialty bed. |
| Duration to Detect Patient Movement | When real-time location tracking (e.g., RFID tracking) is enabled for a patient, this threshold may define the period a sensor may have to detect a patient at a new location before the system updates the patient location. |
| Diagnosis | When a display and/or user has permission to view patient diagnosis information and/or name permission, the system may display the patient's diagnosis in this column. |
| Discharge Timer | The discharge timer may display the number of hours and minutes between (1) when the Physician Order discharge milestone was set for a patient and (2) when the patient was discharged. If the patient's status c hanges from "Pending" or "Confirmed Discharge" to any other status, the system may stop the timer. |
| Home Location | The bed that the patient is assigned to for this hospital stay. |
| Require Bed Assignment for Occupancy | When this setting is enabled, a bed that has been previously assigned to a patient may be marked as occupied by that patient if the patient has been detected in that bed for at least the number of seconds specified in Duration to Detect Patient Movement. |
| Hand Hygiene Index (HHI) | The HHI may be a numeric representation of how closely staff members comply with appropriate hand hygiene practices around the patients who are associated with a unit or with a specific location within a unit. The HHI column shows the Hand Hygiene Index for a specific location or bed. The HHI is tracked through monitoring the movement of staff tags and the use of gel or soap holders affixed with hand hygiene monitors. |
| Hospital Service | The type of treatment or surgery that the patient is or will be receiving (e.g., Oncology, Obstetrics, or |

TABLE 1-continued

| Column | Description |
| --- | --- |
| | Cardiology). |
| Isolation Indicator | If this column is included in the list view, the heading will appear as a shield icon. For every patient in isolation, a shield icon will appear in the column. This is a way to see at a glance which patients are in i solation. |
| Level of Care | The degree of care that the patient requires (e.g., Critical, Intermediate). |
| Med Rec # | The patient's medical record number. In some embodiments, this number may be a sensitive field that is not displayed on public displays. |
| Obs @ | If observation time has been set already for the patient, the system may show the date and time that observation started in this column. If not, then the system may configure the column to display "- -". |
| Occpd Timer | Amount of time between (1) when the patient was marked ready to move and a bed was assigned and cleaned and (2) when the patient began to occupy the bed. Time may be displayed in hh:mm format. For example, if the patient was marked ready to move and the bed to which the patient was to be moved was assigned and cleaned at 10:00 AM and then the patient began to occupy the bed at 10:30 AM, then the Occpd Timer column may display 00:30. |
| Orders | The system may display columns for types of orders (e.g., Lab, Radiology, Medication, or Other). "Other" may include any clinical order that is not a lab or radiology order (e.g., EKG or Pain Assessment). The column headings may have icons to represent the order type. |
| Origin Unit | The unit associated with the request to place the patient. For example, if the patient is being transferred, this may be the unit that the patient is being transferred from. If the patient does not have an open placement request, then this column may be blank. |
| Ready to Move (RTM) Timer | The system may display (e.g., in a patient row) the number of hours and minutes between when the patient's placement request was activated and when the patient was marked "ready to move" to a bed. If the patient is not marked ready to move to a bed within a pre-determined amount of time set in the Administration Tool component, then the system may change the background of the Ready to Move Timer background color from green to yellow. If the background color changes to yellow and then another pre-determined amount of time passes and the patient is still not marked ready to move, the background color may change to red. |
| Referring Physician | The physician who referred the patient for care. |
| Requested | This column displays the date and time that a bed is needed for the patient. When the patient does not have an open placement request, the system may display a blank cell in this column. When a placement request for the patient has been activated, the system may display a date and time in bold and/or green. The system may display the date and time in red when a placement request for the patient is not currently activated. |
| Spec Location | If the patient currently has a procedure in progress, the system may display the bed that the patient is assigned to for the procedure as the Spec Location. |
| Target Unit | The preferred unit in which to place the patient. |
| Transport Status | If a patient who appears in a patient row of the list view has an active transport job, the status of the patient's earliest active job appears in the Transport Status column. |
| Visit Number | Visit Numbers are codes generated by the system that identify each of the patient's hospital stays. The visit number is used in conjunction with the medical record number to identify the patient. |

FIG. 6C illustrates an example of a caregiver assignment graphical user interface. In some embodiments, computer terminal 140 may generate and display the caregiver assignment graphical user interface. In some embodiments, the graphical user interface may streamline and optimize the process of assigning caregivers to beds and in house patients associated with the beds. In some embodiments, the graphical user interface may display the result of a computer-implemented, automated caregiver assignment process performed using one or more of the processes disclosed herein. An embodiment includes functionality to assign and manage permanent employees as well as temporary or agency caregivers, including caregiver types beyond nurses and assistants, and caregivers are not locked into a caregiver type. For example, nurses can be assigned to beds/patients as case managers, assistants, etc., and more than one caregiver can be assigned to a bed/patient. As shown in FIG. 6C, computer terminal 140 may generate a graphical user interface that correlates nurses, case managers, and assistants associated with different locations in a facility such as hospital rooms. The graphical user interface may display real-time scheduling information compiled from multiple scheduling systems, and display assignment information in an interface that is easy to read quickly. In some embodiments, the graphical user interface may include interactive buttons or links to provide additional data associated with the assignments, upon selection by a user. In some embodiments, the graphical user interface may display information associated with the caregivers, such as phone assignment information received from a phone number database.

FIG. 6D illustrates an example of a caregiver assignment menu graphical user interface. In some embodiments, computer terminal 140 may generate and display the graphical user interface based on compiled data received from networked computer systems, and based on further processing to generate displayed information. An embodiment provides for assignment process optimization. In some embodiments, the graphical user interface may allow a user such as a charge nurses and health unit clerks to complete caregiver assignments in a single user interface. The graphical user interface may include one or more buttons for selecting a shift for display, such as the Shift 1 and Shift 2 buttons illustrated in FIG. 6D. In some embodiments, the graphical user interface may display scheduling information automatically collected and processed from one or more networked computer systems or databases, such as a scheduling information database.

Figure 6E:
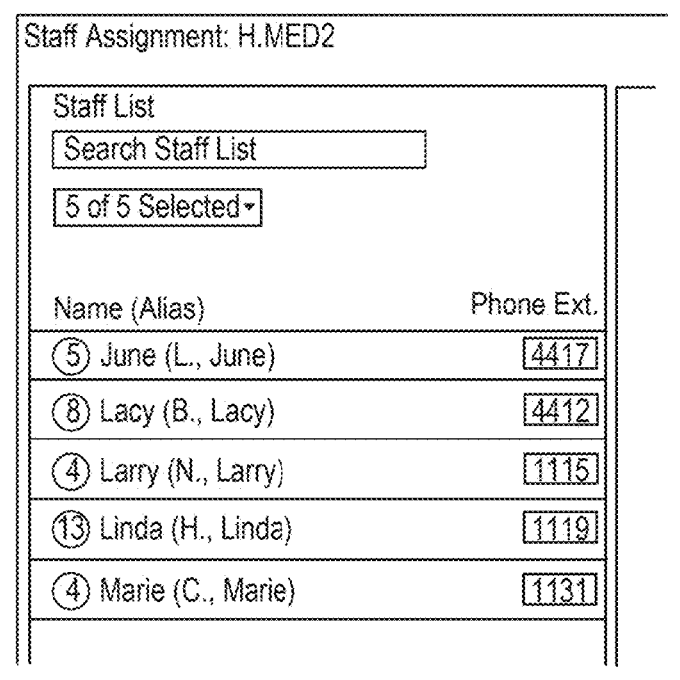

FIG. 6E illustrates a phone assignment view graphical user interface. In some embodiments, computer terminal 140 may generate and display the graphical user interface. The graphical user interface may provide for flexibly assigning assets to caregivers. For example, the graphical user interface may allow a user to select from available caregivers and available assets, and assign assets to caregivers. In the example shown, telephone extensions are assigned to caregivers. In some embodiments, one or more computer systems disclosed herein may automatically assign assets to caregivers using one or more rule sets or assignment algorithms. Because caregivers may not use the same asset on each shift, the present embodiments provide efficient assignment of assets such as phones to each caregiver for each. In some embodiments, the phone assignments may be automatically processed and provided for display in one or more graphical user interfaces. In the example shown, the phone/asset assignment is displayed directly within the caregiver name field for each bed/patient assignment.

Figure 6F:
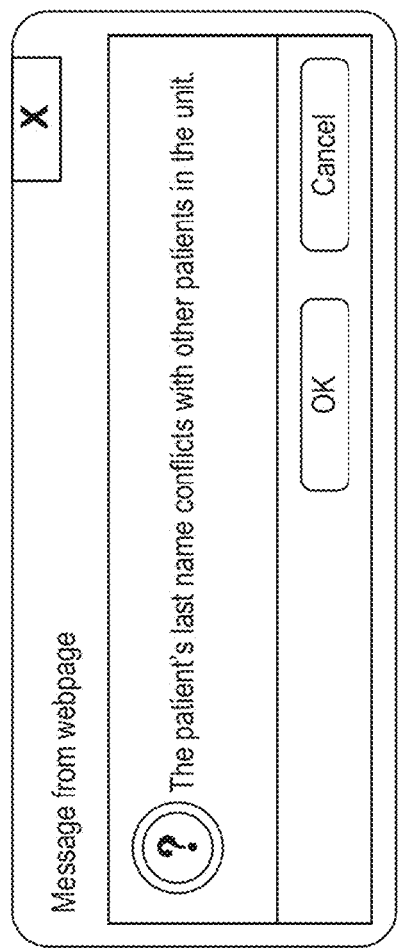

FIG. 6F illustrates an example "same name" alert graphical user interface. In some embodiments, computer terminal 140 may generate and display the graphical user interface. In some embodiments, the graphical user interface may appear as a pop-up superimposed on the graphical user interface for an application. In other embodiments, the graphical user interface may appear in a portion of a graphical user interface. In some embodiments, the graphical user interface may appear when a processor, such as computer terminal 140, determines that two or more patients with the same last name were admitted to beds on the same unit of a facility, such as a hospital unit. In some embodiments, a same name alert may be automatically generated when the system determines that patients who are targeted to a facility unit or assigned to a bed in a unit have a last name that matches another patient currently associated with the same unit or bed. In some embodiments, the same name alert may ensure that patients with the same last name are not placed in the same unit before the system generates one or more commands to move a patient or take other actions associated with the move. Furthermore, the graphical user interface may appear to promptly inform a user of the detected same-name occurrence.

FIG. 6G illustrates a transport equipment return job graphical user interface. In some embodiments, computer terminal 140 may generate and display the graphical user interface. The graphical user interface may display interactive information associated with transport equipment return jobs, such as requests to move certain assets around a facility. In some embodiments, the graphical user interface may provide a user with the ability to instruct the system to generate one or more notifications or workflows associated with returning equipment to the origin of a transport job, or returning equipment to a location other than the origin of the original transport job. In some embodiments, the graphical user interface may provide one or more input selections for instructing the computer system to generate notifications and workflows for generating one more reports indicating a frequency of occurrence. The graphical user interface may allow the equipment to be tracked and returned, and also provide a display of the time taken to return the equipment facilitating more accurate accounting for time. In the example shown in FIG. 6G, a wheelchair was used to move patient name Test 1, from room 1104 bed 3, to room 6C01 bed 2. The graphical user interface may provide one or more selection buttons such as "roundtrip," "equipment return," "delay job" (if in progress), "cancel job" (if in progress), and "request assist." In some embodiments, selection of one or more of the selection buttons may instruct the computer system to generate one or more notifications and workflows associated with the respective button.

Figure 7:
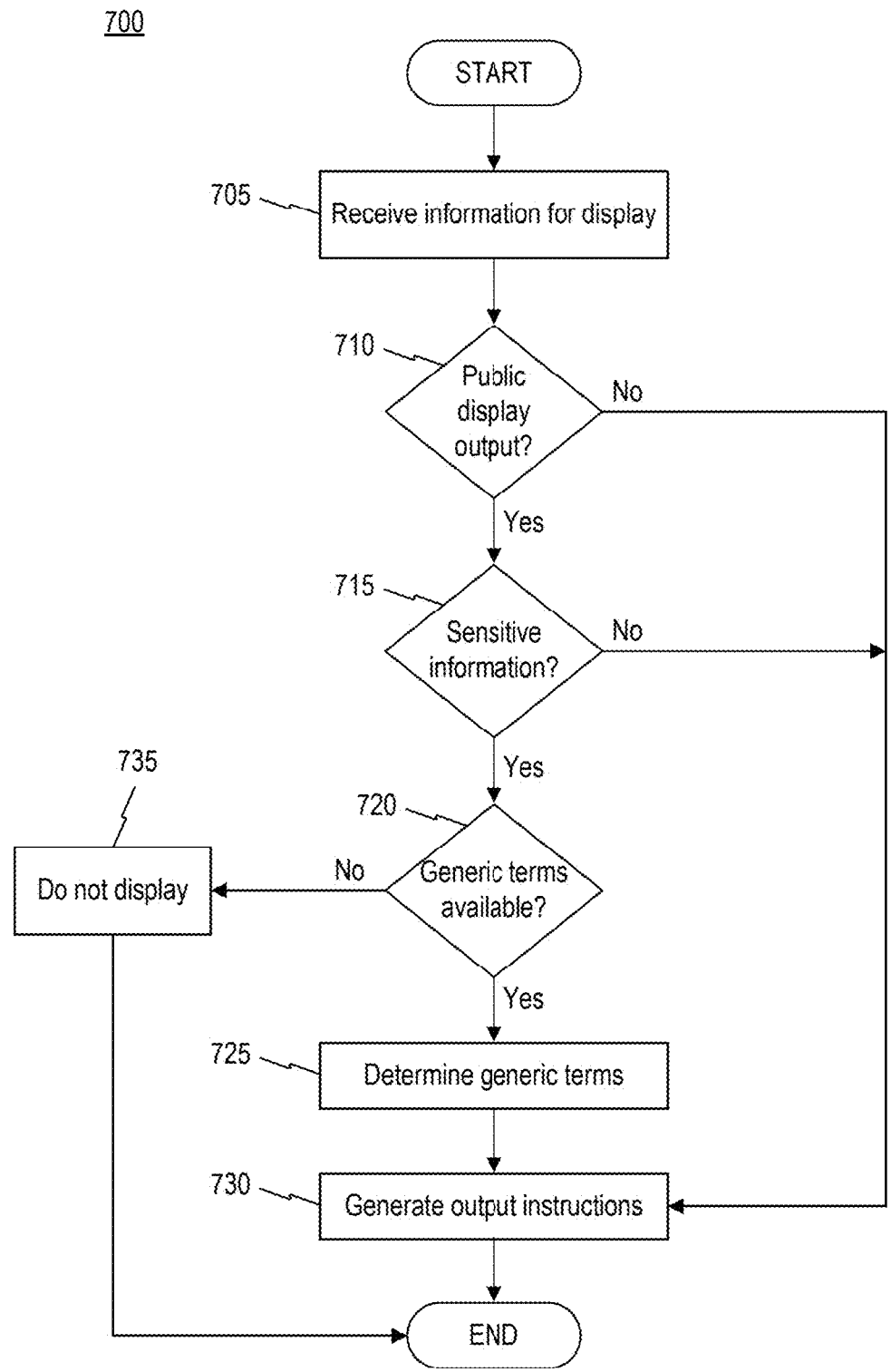
FIG. 7 is a flowchart of an example of a process for identifying and screening sensitive information for display, consistent with embodiments of the present disclosure.

FIG. 7 is a flowchart of an exemplary display screening process 700. Process 700 is described herein as being performed by computer terminal 140, private display 514, and public display 520. However, other displays and computing equipment may be used to perform all, or portions of, process 700. In some embodiments, user device 120, facility server 130, network server 160, third-party server 170, and/or database 180 may perform steps of process 700.

Process 700 may describe steps for updating user interface 600 based on new information from sensors or networked servers. For example, computer terminal 140 may generate two versions of user interface 600: one for public display (e.g. on public display 520) and one for private display (e.g., on private display 514). While a private display may not be subject to regulatory restrictions (e.g., HIPAA requirements), public displays may need to be censored to remove identifying information and specific patient treatment information. Accordingly, computer terminal 140 may perform process 700 when receiving information for display to ensure that public displays of user interface 600 comply with regulatory requirements.

Process 700 may begin with step 705 when computer terminal 140 receives information for display. In some embodiments, computer terminal 140 may receive patient information from a computing device, such as network server 160, facility server 130, administrator terminal 145, user device 120, and/or third-party server 170. In some embodiments, patient information may include patient intake and discharge requests from network server 160 (e.g., a patient placement server). Patient information may include status updates from nursing stations (e.g., user device 120), service processing (e.g., lab results, pharmacy orders, transport requests), staffing servers (e.g., nurse assignments, attending physician), and patient characteristics (e.g., illness, medications, fall risk).

In step 710, computer terminal 140 may determine whether the information received in step 705 pertains to a user interface that is publicly displayed. In some embodiments, computer terminal 140 may determine whether a connection exists to public display 520. Computer terminal 140 may receive display identifiers indicating the location, position, and/or size of available displays. Computer terminal may use display characteristics to determine whether a display is public (e.g., step 710, "yes") or whether a display is a private display that hospital visitors may not be able to view (e.g., step 710, "no"). For example, when a display is located behind a nursing station desk or includes viewing security mechanisms, computer terminal may determine that the display is a private display and proceed to step 730. When a display is over 30 inches in width, computer terminal 140 may determine that the display is a public display and proceed to step 715.

In step 715, computer terminal 140 may determine whether the information received in step 705 includes sensitive information. In some embodiments, when computer terminal computer determines that a display is a public display (e.g., step 710, "yes"), terminal 140 may query a server to verify HIPAA requirements for specific information. Computer terminal 140 may compare the received information with the HIPAA requirements to determine if the information is suitable for public display. Computer terminal may determine that no information is sensitive and proceed to step 730. However, when the HIPAA requirements indicate that the information is sensitive and not suitable for public display (e.g., step 715, "yes"), process 700 may proceed to step 720.

In step 720, computer terminal 140 may determine whether the information received in step 705 may be expressed using generic terms. Computer terminal may compare sensitive patient record information with known generic equivalents. For example, computer terminal 140 may query a database with the sensitive information identified in step 715. Based on the query, computer terminal 140 may receive HIPAA-compliant generic terms that abstract away details of the patient information. Rather than indicating that a patient has a particular disease, a HIPAA compliant database may indicate a class of disease or relevant characteristics of the disease that need not be kept private.

When computer terminal 140 determines that no generic terms exist (e.g., step 720; no), computer terminal 140 may prevent the display of information in step 735. When it is not possible for computer terminal 140 to convey patient information in any form, regardless of the level of abstraction, computer terminal 140 may generate instructions to prevent the display of the sensitive information.

Responsive to determining that generic terms exist (step 720), computer terminal 140 may determine generic terms to use for display in step 725. Computer terminal 140 may aggregate and organize HIPAA-equivalent database results. For example, computer terminal 140 may identify redundant generic descriptors and elect a single generic descriptor from the group.

In step 730, computer terminal 140 may generate output instructions. When the received information is for private display (e.g., step 710, "no") or does not include sensitive information (e.g., step 715, "no"), computer terminal will generate instructions to display the received information in a nursing station user interface. When generic terms are determined for sensitive patient information, output instructions include the selected generic terms.

Output instructions may include a display identifier and display data. In some embodiments, computer terminal may include connections to multiple private and multiple public displays. To ensure that private information is not shown on public displays, the private display data may be transmitted with the display identifier for a private display. To further provide redundant checks on the display, computer terminal 140 may include a check sum value that the display must use to validate that it is a public or private display.

Figure 8A:
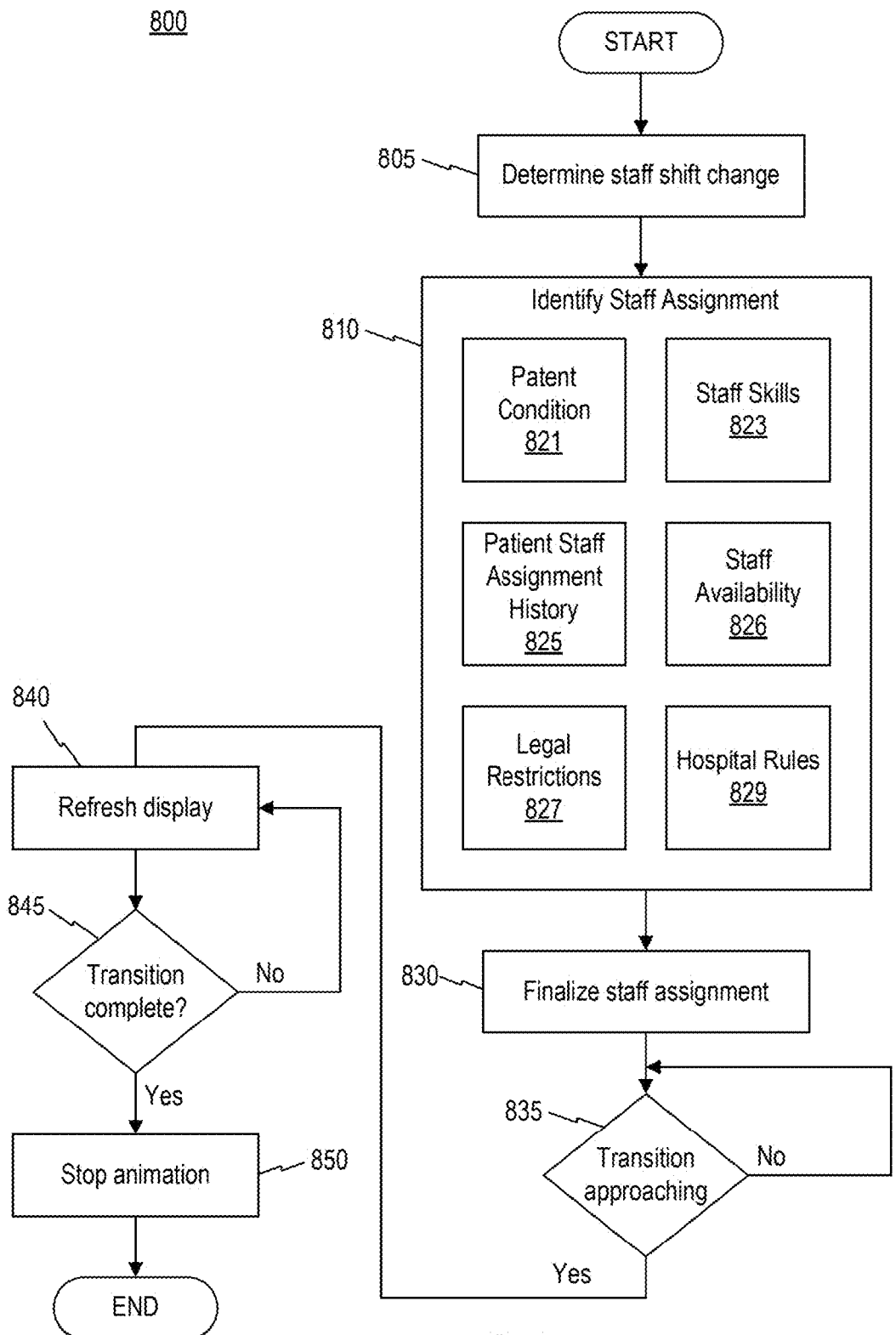
FIG. 8A is a flowchart of an example of a process for assigning a caregiver to a patient, consistent with embodiments of the present disclosure.

FIG. 8A is a flowchart of an exemplary caregiver assignment process 800. Process 800 is described herein as being performed by computer terminal 140, private display 514, and public display 520. However, other displays and computing equipment may be used to perform all, or portions of, process 800. In some embodiments, user device 120, facility server 130, network server 160, third-party server 170, and/or database 180 may perform steps of process 800.

Process 800 may describe steps for determining staff assignments and updating user interface 600 to display the updated assignments. For example, a nursing shift may end soon. Because patients may be admitted to and discharged from a hospital based on extraneous, unplanned factors, nurse assignments may be advantageously determined proximate to the beginning of a shift. Computer terminal 140 may determine assignments for the nurses starting on the next shift based on patient data aggregated from prior shifts and current patient load using process 800. Further, computer terminal 140 may update interface 600 to convey the change in nursing assignments.

Process 800 may begin with step 805 when computer terminal 140 determines that a staff shift end approaches. In some embodiments, computer terminal 140 may receive staff work schedules from third-party server 170. Computer terminal 140 may also determine a threshold window for beginning staff assignment calculations. For example, user preferences may indicate that thirty minutes prior to a shift change, computer terminal 140 should display staff assignments for the upcoming new shift. When the threshold is reached, process 800 may progress to step 810.

In step 810, computer terminal 140 may identify staff assignments for the upcoming shift. In some embodiments, computer terminal 140 may utilize patient and staff information to prepare favorable staff assignments to maximize patient satisfaction. For example, computer terminal may receive data from database 180, network server 160 and third-party server 170 to make patient-staff pairings.

In some embodiments, computer terminal 140 may receive patient and staff information to facilitate positive matching between caregivers and patients. Computer terminal 140 may receive patient information, such as patient conditions 821. In some embodiments, patient information may include the current treatment that the patient is undergoing, any illnesses or known diseases, an age of the patient, and a gender for the patient. Computer terminal may receive staff skills 823, indicating staff specialties. For example, staff skills 823 may indicate that a particular staff member has experience with elderly patients, has specialized training to recover stroke victims, or has received extensive positive feedback for a bedside manner. Computer terminal 140 may match a patient with a caregiver by identifying complementary patient conditions 821 with staff skills 823. For example, if the patient experienced a stroke and is elderly, and a staff member has specialized training for handling elderly stroke victims, computer terminal 140 may identify them as a good match.

In some embodiments, computer terminal 140 may emphasize continuity of care when identifying staff assignments. Computer terminal 140 may utilize patient staff assignment history 825 and staff availability 826 when performing step 810. For example, computer terminal 140 may analyze assignment history 825 to determine that patient John Smith has had nurse Jackie assigned for the past three evenings, Monday through Wednesday. Based on staff availability 826, computer terminal may determine that Jackie is scheduled to work Thursday evening as well. Computer terminal 140 may assign Jackie to care for John Smith to ensure that John Smith is familiar with his caretakers.

In some embodiments, computer terminal 140 may ensure that staff assignments comply with local rules and hospital policies. Computer terminal 140 may validate staff assignments against legal restrictions 827 and hospital rules 829. For example, legal restrictions 827 and hospital rules 829 may include limits on the nurse to patient ratio for a nursing unit. Other rules may include required certifications for nurses to care for patients with certain conditions.

In step 830, computer terminal 140 may finalize the staff assignment. After matching patient conditions, ensuring continuity of care, and/or validating the staff assignment to relevant rules, computer terminal 140 may publish a staff assignment. For example, computer terminal 140 may transmit a finalized staff assignment record to database 180.

In step 835, computer terminal 140 may determine if the transition period is approaching. Computer terminal 140 may receive a predefined period of time prior to the shift transition at which the new assignment should be displayed. For example, computer terminal 140 may receive settings indicating that 15 minutes prior to a shift change, the new nurse assignments are to be displayed. Prior to approaching this threshold interval (e.g., step 835, "no"), computer terminal 140 may revalidate the staff assignment and repeat step 835. For example, computer terminal 140 may determine if any updated information has been received and whether the information materially affects the staff assignment. When the threshold time period is reached (e.g., step 835, "yes"), such as when the current time is less than 15 minutes prior to the shift change, process 800 may continue to step 840.

In step 840, computer terminal 140 may refresh interface 600. In some embodiments, computer terminal may refresh the display by animating information on the display to reflect newly-received data. Computer terminal 140 may generate instructions indicating the new shift of staff assignments and how the staff assignments should be highlighted. For example, computer terminal 140 may transmit instructions to highlight and alternate between the ending shift and the new shift assignments. Computer terminal may transmit instructions to highlight nurse data 640 with a yellow background and bold font. The instructions of computer terminal 140 may also cause interface 600 to alternate displaying the ending shift and the current shift with a frequency of one hertz.

In step 845, computer terminal 140 may determine if the shift transition is complete. Computer terminal 140 may determine if the current time exceeds the threshold period for presenting the animation. For example, computer terminal 140 may receive preferences indicating that the shift assignments should be displayed ten minutes prior to and ten minutes after the shift transition. For a 10:30 PM shift change, computer terminal 140 may determine at 10:36 PM that the shift change is not complete (e.g., step 845, "no") and continue to animate the display (step 840). At 10:40 PM computer terminal 140 may determine that the shift transition is complete (e.g., step 845, "yes"), and proceed to step 850.

In step 850, computer terminal 140 may end the animation of interface 600. Computer terminal 850 may generate instructions to revert the display of interface 600 to normal, unstyled font. The instructions of computer terminal 850 may also remove any highlighting or animation in interface 600.

Computer terminal 140 may repeat process 800 for each shift change. In embodiments where not all nurses change shift at the same time, computer terminal may only animate portions of interface 600 corresponding to patients with a nurse shift change.

Figure 8C:
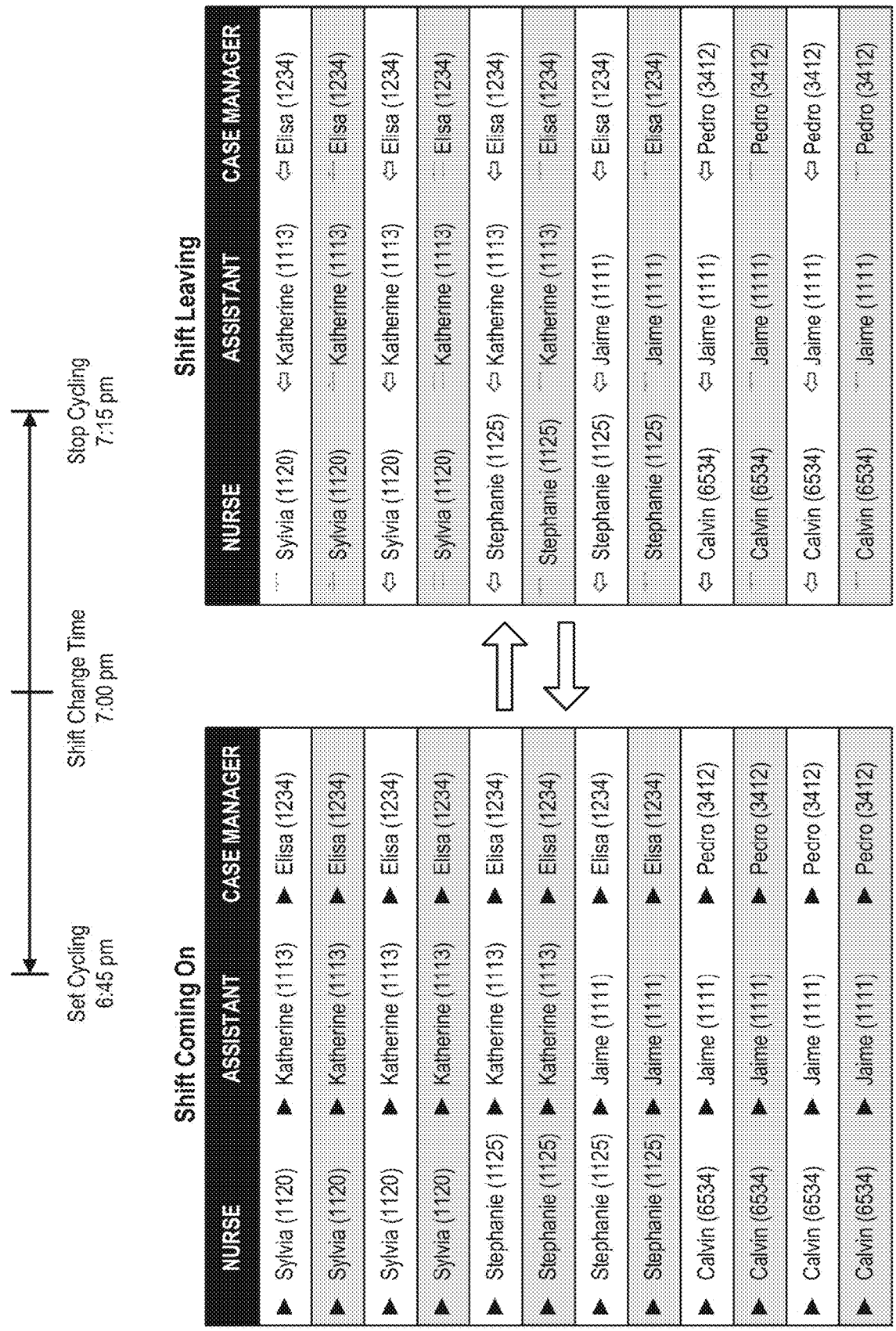
FIG. 8C illustrates an example shift cycle screen graphical user interface, consistent with embodiments of the present disclosure.

FIG. 8C illustrates an example of a caregiver history view graphical user interface. In some embodiments, computer terminal 140 may generate and display the graphical user interface during one or more steps of process 800, to provide for increased continuity of care. Patient outcomes and satisfaction may improve when patients receive consistent care, which is often achieved by assigning the same nurses throughout the patient's stay. The disclosed systems and graphical user interfaces may achieve these goals by allowing a user, such as a charge nurses or unit clerks, to assign the same nurses to patients that they have previously taken care of. Computer terminal 140, or another processor disclosed herein, may determine a history of caregivers previously assigned to particular patients, and provide the caregiver history in the graphical user interface to suggest caregivers for assigning in future shifts for particular patients. In some embodiments, a processor may automatically assign caregivers based on previous assignments and scheduling information.

FIG. 8C illustrates an example shift cycle graphical user interface. In some embodiments, computer terminal 140 may generate and display the graphical user interface during one or more steps of process 800, to facilitate patient handoff from one caregiver to another. In some embodiments, the graphical user interface may allow a user, such as a charge nurse or staff nurse, to quickly and efficiently see multiple caregiver-to bed assignments for the current shift and the next shift, to facilitate a proper handoff and knowledge transfer between shifts.

In some embodiments, computer terminal 140 may generate and display an animated graphical user interface that displays animated elements corresponding to real-time information updates, to present large amounts of data efficiently and effectively to a viewer of the graphical user interface. For example, an animated graphical user interface may include arrows that cycle between red arrows signaling the leaving shift and green arrows signaling the shift coming on duty. In some embodiments, the time when the cycling begins may be configured by a user or predefined rules. For example, cycling may be set by a user or predefined rule to begin fifteen minutes prior to the new shift start time and continue through fifteen minutes after the actual shift start time. At this setting the cycling will continue for a half hour during the shift change.

FIG. 9 is an illustration of an exemplary staff history report query interface 900. Interface 900 may allow computer terminal 140 to receive data identifying a particular patient or time period during which care was provided. Computer terminal 140 may query database 180 based on inquiry information received using interface 900. For example, interface 900 may include fields to receive information identifying a particular patient, such as user interface elements 910 and 920. Computer terminal 140 may receive text strings corresponding to a patient's name or identifier (e.g. Medical Record Number (MRN) or Visit Number) using user interface elements 910 and 920.

Interface 900 may include fields to enter the beginning and end of a period of time during which care was provided, such as user interface elements 930 and 940. Computer terminal 140 may narrow the query and, hence, reduce the necessary processing resources when temporal bounds (e.g., dates and/or times) are received in user interface elements 930 and 940.

Interface 900 may include fields to receive data indicating particular care descriptors, such as user interface elements 950 and 960. Computer terminal 140 may receive the identifier of a particular nursing unit to isolate results when a patient transferred between multiple nursing units during his or her stay.

Computer terminal may generate a report using the information resulting from the query of computer terminal 140, such as when a selection of user interface element 970 is received. Responsive to receiving a selection of user interface element 970 from an input device, computer terminal 140 may generate a query to receive staff assignment histories for the requested patients, time periods, and care information.

Additional fields (not shown) may allow for further query options. For example, computer terminal 140 may receive Nursing Unit(s), Patient(s), Staff Member(s), and/or Staff Assignment Type(s) to define the bounds of a staff history report.

Figure 10:
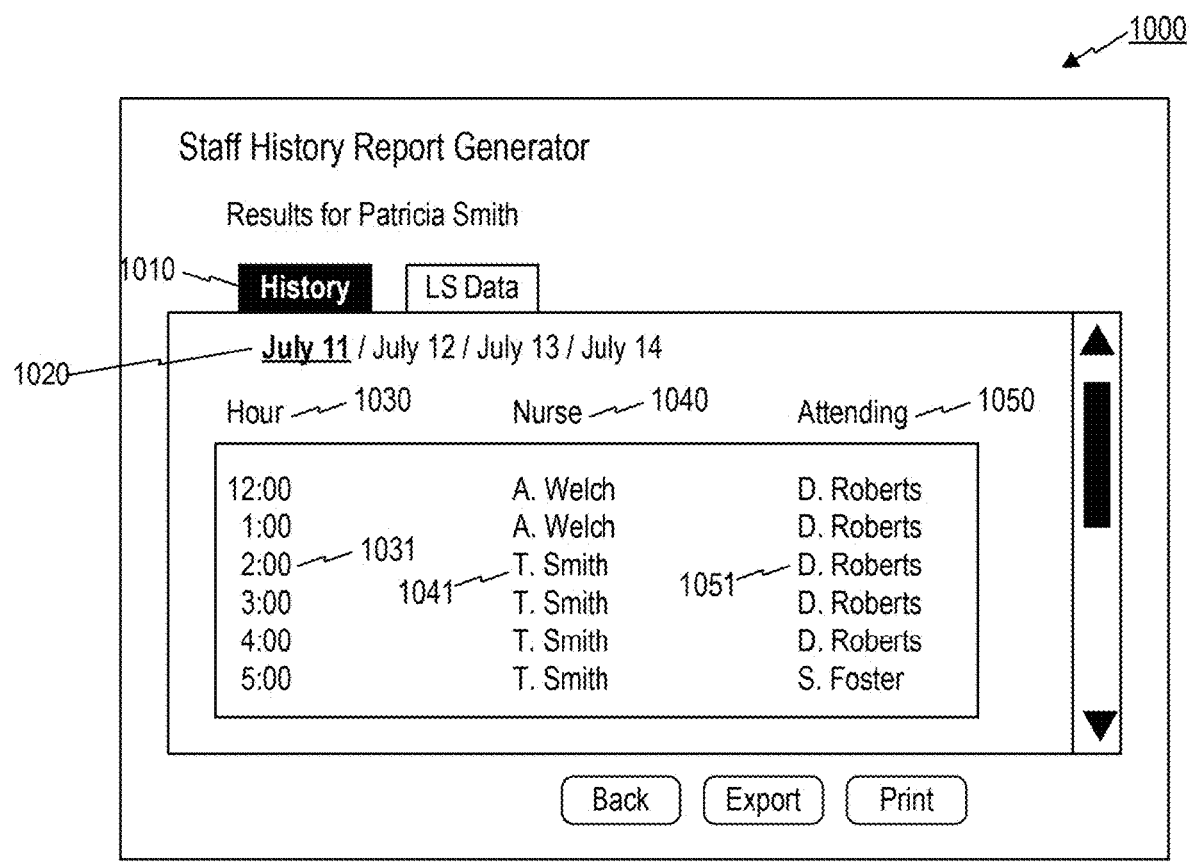

FIG. 10 is an illustration of an exemplary staff history report generator interface 1000. In some embodiments, computer terminal 140 may generate interface 1000 to include tabular selection regions 1010 to access different care data. For example, interface 1000 may show a patient's caregiver assignment history in one pane and allow the "last seen" data to be shown in a separate tabbed pane. The last seen pane (not shown) may display more detailed last seen data, including duration of visit and visit narratives.

Within the history pane, interface 1000 may present sortable columns for hour data 1030, nurse data 1040, and attending physician data 1050. Within each column, interface 1000 may provide selection regions 1031, 1041, and 1051 to select column data to display additional detail. For example, when selection region 1031 is selected by input, computer terminal 140 may provide data in 10 minute increments for the selected hour. When computer terminal 140 receives input selecting selection areas 1041 or 1051, computer terminal 140 may query database 180 to provide corresponding biographical data to interface 1000 for display. When a query spans multiple days, interface 1000 may divide information for each day, such as using date selection region 1020.

Interface 1000 may also include additional selection regions to permit computer terminal 140 to receive requests to generate print instructions or generate files for download.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A computerized system for automatic generation of a real-time patient and bed status grid including dynamic discharge status graphical indicators, the system comprising:
   at least one networked processor; and
   a storage medium comprising instructions that, when executed, cause the at least one networked processor to automatically perform the operations of:
      generating instructions for displaying an interactive graphical user interface for a station display in communication with the at least one networked processor, the interactive graphical user interface showing a grid of real-time statuses for patients and beds in a medical facility, and for each of a plurality of patients, the grid simultaneously displaying:
         graphical care progress indicators associated with a patient identifier associated with each of the plurality of patients, and
         a percentage completion of a set of milestone tasks determined using one or more remaining milestone tasks, wherein the percentage completion of the set of milestone tasks is displayed as a bar graph showing an amount of fill in the bar corresponding to the percentage completion;
      receiving, via a network, real-time status information with the patient identifier or a bed status identifier,
      prior to patient arrival, loading bed status information which indicates an availability of a bed for patient assignment,
      loading a discharge milestone plan corresponding to the patient identifier, the milestone plan including a predetermined set of milestone tasks to be completed before releasing the patient, and an initial estimated discharge time period associated with the set of milestone tasks,
      responsive to receipt of real-time status information corresponding to one of the milestone tasks:
         determining whether the real-time status information indicates completion of the milestone task based at least in part on one or more interim progress updates and a set of rules associated with one or more patient conditions,
         updating the discharge milestone plan based on the real-time status information to indicate completion of the milestone task and one or more remaining milestone tasks,
         automatically calculating a revised estimated discharge time based on the initial estimated discharge time period, a current time, and a time period associated with the completed milestone task or the one or more remaining milestone tasks, and
         automatically generating interface update information reflecting the revised estimated discharge time, and a graphical representation of the discharge milestone plan status, the graphical representation depicting an amount of completed milestone tasks compared to the one or more remaining milestone tasks in the updated milestone plan;
      responsive to receipt of real-time status information corresponding to the status of the patient bed availability:
         determining whether the real-time status information indicates that the bed is available for patient assignment,
         assigning an incoming patient to an available bed based on the real-time status information,
         updating the bed status identifier to indicate that the patient-assigned bed is no longer available,
         automatically generating the interface update information reflecting that the patient-assigned bed is no longer available; and
      providing the generated interface update information for output in the real-time patient tracking interface on the station display.

2. The system of claim 1, wherein
   receiving the real-time status information with the patient identifier includes receiving electronic lab results and a patient identifier via the network from a third-party server, and
   determining that real-time status information indicates completion of one of the milestone tasks includes determining that the electronic lab results include metrics that fall within a predetermined range corresponding to completion of an examination.

3. The system of claim 1, wherein
   the set of milestone tasks includes at least one required milestone task and at least one optional milestone task, and
   calculating the revised estimated discharge time is based on the at least one required task and does not take into account the at least one optional milestone task.

4. The system of claim 3, wherein the at least one required milestone task and the at least one optional milestone task are based on a predetermined discharge protocol associated with the patient identifier.

5. The system of claim 1, further comprising:
   responsive to receipt of real-time status information corresponding to one of the milestone tasks, calculating a percentage completion of the milestone plan based on the updated milestone plan; and generating, as part of the interface update information, a graphical symbolic representation of the calculated percentage.

6. The system of claim 5, wherein calculating the revised estimated discharge time is further based on the percentage completion of the discharge milestone plan.

7. A computerized method for automatic generation of a real-time patient and bed status grid including dynamic discharge status graphical indicators, the method comprising:
generating instructions for displaying an interactive graphical user interface for a station display in communication with the at least one networked processor, the interactive graphical user interface showing a grid of real-time statuses for patients and beds in a medical facility, and for each of a plurality of patients, the grid simultaneously displaying:
graphical care progress indicators associated with a patient identifier associated with each of the plurality of patients, and
a percentage completion of a set of milestone tasks determined using one or more remaining milestone tasks, wherein the percentage completion of the set of milestone tasks is displayed as a bar graph showing an amount of fill in the bar corresponding to the percentage completion;
receiving, by at least one networked processor via a network, real-time status information with the patient identifier or a bed status identifier;
prior to patient arrival, loading bed status information which indicates an availability of a bed for patient assignment,
loading a discharge milestone plan corresponding to the patient identifier, the milestone plan including a predetermined set of milestone tasks to be completed before releasing the patient, and an initial estimated discharge time period associated with the set of milestone tasks;
responsive to receipt of real-time status information corresponding to one of the milestone tasks:
determining whether the real-time status information indicates completion of the milestone task based at least in part on one or more interim progress updates and a set of rules associated with one or more patient conditions;
updating the discharge milestone plan based on the real-time status information to indicate completion of the milestone task and one or more remaining milestone tasks;
automatically calculating a revised estimated discharge time based on the initial estimated discharge time period, a current time, and a time period associated with the completed milestone task or the one or more remaining milestone tasks; and
automatically generating interface update information reflecting the revised estimated discharge time, and a graphical representation of the discharge milestone plan status, the graphical representation depicting an amount of completed milestone tasks compared to the one or more remaining milestone tasks in the updated milestone plan;
responsive to receipt of real-time status information corresponding to the status of the patient bed availability:
determining whether the real-time status information indicates that the bed is available for patient assignment,
assigning an incoming patient to an available bed based on the real-time status information,
updating the bed status identifier to indicate that the patient-assigned bed is no longer available,
automatically generating the interface update information reflecting that the patient-assigned bed is no longer available; and
providing the generated interface update information for output in the real-time patient tracking interface on the station display.

8. The method of claim 7, wherein
receiving the real-time status information with the patient identifier includes receiving electronic lab results and a patient identifier via the network from a third-party server, and
determining that real-time status information indicates completion of one of the milestone tasks includes determining that the electronic lab results include metrics that fall within a predetermined range corresponding to completion of an examination.

9. The method of claim 7, wherein
the set of milestone tasks includes at least one required milestone task and at least one optional milestone task, and
calculating the revised estimated discharge time is based on the at least one required task and does not take into account the at least one optional milestone task.

10. The method of claim 9, wherein the at least one required milestone task and the at least one optional milestone task are based on a predetermined discharge protocol associated with the patient identifier.

11. The method of claim 7, further comprising:
responsive to receipt of real-time status information corresponding to one of the milestone tasks, calculating a percentage completion of the milestone plan based on the updated milestone plan; and
generating, as part of the interface update information, a graphical symbolic representation of the calculated percentage.

12. The method of claim 11, wherein calculating the revised estimated discharge time is further based on the percentage completion of the discharge milestone plan.

13. A non-transitory computer-readable medium storing instructions which, when executed, cause at least one networked processor to perform a method for automatic generation of a real-time patient and bed status grid including dynamic discharge status graphical indicators, the method comprising:
generating instructions for displaying an interactive graphical user interface for a station display in communication with the at least one networked processor, the interactive graphical user interface showing a grid of real-time statuses for patients and beds in a medical facility, and for each of a plurality of patients, the grid simultaneously displaying:
graphical care progress indicators associated with a patient identifier associated with each of the plurality of patients, and
a percentage completion of a set of milestone tasks determined using one or more remaining milestone tasks, wherein the percentage completion of the set of milestone tasks is displayed as a bar graph showing an amount of fill in the bar corresponding to the percentage completion;
receiving, by at least one networked processor via a network, real-time status information with the patient identifier or a bed status identifier;

prior to patient arrival, loading bed status information which indicates an availability of a bed for patient assignment, loading a discharge milestone plan corresponding to the patient identifier, the milestone plan including a predetermined set of milestone tasks to be completed before releasing the patient, and an initial estimated discharge time period associated with the set of milestone tasks;

responsive to receipt of real-time status information corresponding to one of the milestone tasks:
  determining whether the real-time status information indicates completion of the milestone task based at least in part on one or more interim progress updates and a set of rules associated with one or more patient conditions;
  updating the discharge milestone plan based on the real-time status information to indicate completion of the milestone task and one or more remaining milestone tasks;
  automatically calculating a revised estimated discharge time based on the initial estimated discharge time period, a current time, and a time period associated with the completed milestone task or the one or more remaining milestone tasks; and
  automatically generating interface update information reflecting the revised estimated discharge time, and a graphical representation of the discharge milestone plan status, the graphical representation depicting an amount of completed milestone tasks compared to the one or more remaining milestone tasks in the updated milestone plan;

responsive to receipt of real-time status information corresponding to the status of the patient bed availability:
  determining whether the real-time status information indicates that the bed is available for patient assignment,
  assigning an incoming patient to an available bed based on the real-time status information,
  updating the bed status identifier to indicate that the patient-assigned bed is no longer available,
  automatically generating the interface update information reflecting that the patient-assigned bed is no longer available; and
providing the generated interface update information for output in the real-time patient tracking interface on the station display.

14. The method of claim 13, wherein
receiving the real-time status information with the patient identifier includes receiving electronic lab results and a patient identifier via the network from a third-party server, and
determining that real-time status information indicates completion of one of the milestone tasks includes determining that the electronic lab results include metrics that fall within a predetermined range corresponding to completion of an examination.

15. The method of claim 14, wherein
the set of milestone tasks includes at least one required milestone task and at least one optional milestone task, and
calculating the revised estimated discharge time is based on the at least one required task and does not take into account the at least one optional milestone task.

16. The method of claim 15, wherein the at least one required milestone task and the at least one optional milestone task are based on a predetermined discharge protocol associated with the patient identifier.

17. The method of claim 13, further comprising:
responsive to receipt of real-time status information corresponding to one of the milestone tasks, calculating a percentage completion of the milestone plan based on the updated milestone plan; and
generating, as part of the interface update information, a graphical symbolic representation of the calculated percentage.

18. The method of claim 17, wherein calculating the revised estimated discharge time is further based on the percentage completion of the discharge milestone plan.

19. The system of claim 1, wherein the one or more interim progress updates include one of:
a third-party server indicating that a scan has been processed but is awaiting analysis; or
a computerized IV administration indicating that a patient has completed a percentage of a drug dose.

20. The system of claim 1, wherein the generated interface update information indicates that the patient is ready for discharge after the milestone plan is completed.

21. The system of claim 1, wherein the real-time patient tracking interface further displays support icons indicating support services for patient care.

22. The system of claim 21, wherein the support icons reflect the status of third party care services for the patient.

* * * * *